US 7,945,865 B2

(12) United States Patent
Adachi et al.

(10) Patent No.: US 7,945,865 B2
(45) Date of Patent: May 17, 2011

(54) INFORMATION PROCESSING SYSTEM, INFORMATION PROCESSING APPARATUS, AND METHOD

(75) Inventors: Shinobu Adachi, Osaka (JP); Koji Morikawa, Kyoto (JP)

(73) Assignee: Panasonic Corporation, Osaka (JP)

( * ) Notice: Subject to any disclaimer, the term of this patent is extended or adjusted under 35 U.S.C. 154(b) by 578 days.

(21) Appl. No.: 11/718,108

(22) PCT Filed: Oct. 6, 2006

(86) PCT No.: PCT/JP2006/320102
§ 371 (c)(1),
(2), (4) Date: Apr. 27, 2007

(87) PCT Pub. No.: WO2007/066451
PCT Pub. Date: Jun. 14, 2007

(65) Prior Publication Data
US 2009/0049089 A1    Feb. 19, 2009

(30) Foreign Application Priority Data

Dec. 9, 2005    (JP) .................................. 2005-356428

(51) Int. Cl.
*G06F 17/30*    (2006.01)
*A61B 5/00*    (2006.01)
(52) U.S. Cl. ...................................... 715/863; 715/764
(58) Field of Classification Search .................. 715/764, 715/863
See application file for complete search history.

(56) References Cited

U.S. PATENT DOCUMENTS

| 4,846,190 | A | * | 7/1989 | John | 600/544 |
| 5,137,027 | A | * | 8/1992 | Rosenfeld | 600/544 |
| 2003/0129574 | A1 | * | 7/2003 | Ferriol et al. | 434/362 |
| 2006/0101079 | A1 | | 5/2006 | Morikawa et al. | |

FOREIGN PATENT DOCUMENTS

| JP | 2005-293209 | 10/2005 |
| WO | 03/050782 | 6/2003 |
| WO | 2005/001677 | 1/2005 |

OTHER PUBLICATIONS

International Search Report for corresponding Application No. PCT/JP2006/320102 mailed Dec. 12, 2006.
"Information or Emotion?—Influences of Amount of Information and Rewards on Stimulus-Preceding Negativity (SPN)"; Seirishinrigaku to Seishinseirigaku (or Japanese Journal of Physiological Psychology and Psychophysiololgy); vol. 19, No. 3, 2001.
Toshiro Sasai et al.; "Tayoto Nohakei to Sekigaisen Netsu Gazo Sochi ni yoru Interface Shinri Tokusei no Jikken Kenyu," Correspondences on Human Interface, vol. 1, No. 3; Jun. 17, 1999; p. 17, right column, line 9 to p. 19 left column, line 4. (Listed on International Search Report for Corresponding Application No. PCT/JP2006/320102 submitted on Apr. 27, 2007).

* cited by examiner

*Primary Examiner* — Tadeese Hailu
*Assistant Examiner* — Andrea Leggett
(74) *Attorney, Agent, or Firm* — Renner, Otto, Boisselle & Sklar, LLP

(57) ABSTRACT

A degree of confidence is objectively evaluated without permitting a user's subjective evaluation, and a content to be output is determined based on this evaluation.

An information processing system comprising: an input section for receiving an input from a user; a signal detection section for measuring a signal concerning an event-related potential of electroencephalograms of the user; a determination section for determining a degree of confidence of the user with respect to the input based on an amount of negative shift in the event-related potential during a predetermined period after the input is received; a control section for determining a content to be presented to the user based on the degree of confidence; and an output section for presenting the determined content to the user.

18 Claims, 17 Drawing Sheets

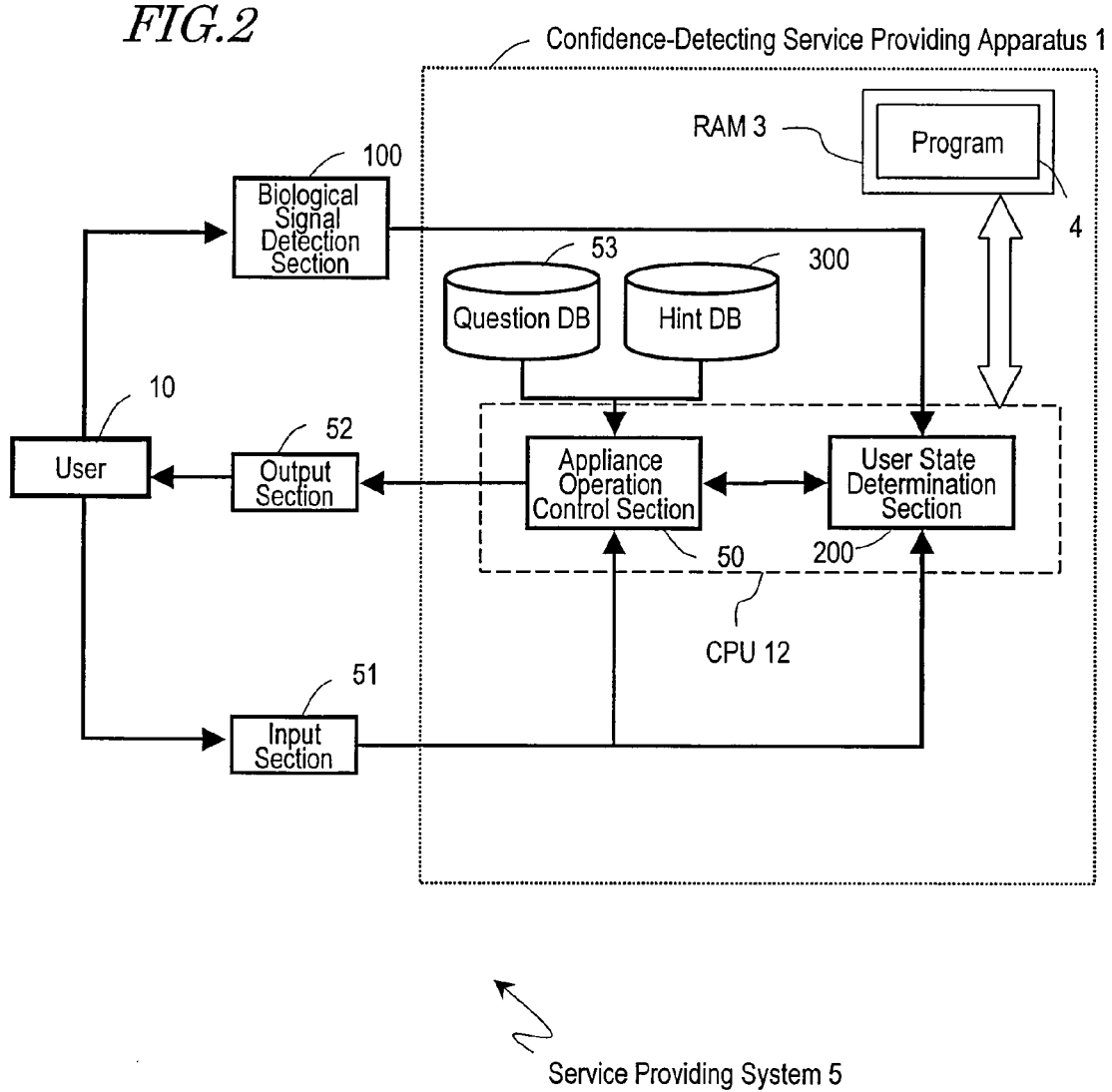

*FIG.3*

| Test | Confident Group | Unconfident Group |
|---|---|---|
| 1 | −0.0259 | 0.0046 |
| 2 | 0.0038 | −0.0128 |
| 3 | −0.0099 | −0.0134 |
| 4 | −0.0043 | 0.0024 |
| 5 | −0.0034 | 0.0048 |
| 6 | −0.0007 | −0.0164 |
| 7 | 0.0028 | 0.0036 |
| 8 | −0.009 | −0.0085 |
| 9 | −0.0146 | 0.0036 |
| 10 | −0.0112 | 0.0012 |
| ... | ... | ... |

*FIG.4*

| | Question | | | | | | | | | Correct Answer | Importance Level |
|---|---|---|---|---|---|---|---|---|---|---|---|
| 1 | Expand $(x-y)^2$ | A | $x^2+y^2$ | B | $X^2-y^2$ | C | $x^2+2xy+y^2$ | D | $x^2-2xy+y^2$ | B | 5 |
| 2 | Who Is the Shogun That Issued the "Shorui-Awaremino-Rei" Orders? | A | Iemitsu | B | Ietsuna | C | Tsunayoshi | D | Ienobu | C | 5 |
| 3 | What does CREDIT Mean? | A | Cash | B | Bank | C | Trust | D | Purchase | C | 3 |
| 4 | Which Book Is the Basis for the Words of the National Anthem "Kimigayo"? | A | Manyoshu | B | Kojiki | C | Nihonshoki | D | Kokinwaka-shu | D | 3 |
| 5 | Which Country does not Belong to the African Continent? | A | Nigeria | B | Kenya | C | Guinea | D | Austria | D | 1 |
| 6 | Which Peninsula Has the Largest Area in Japan? | A | Shimokita Peninsula | B | Shiretoko Peninsula | C | Ise Peninsula | D | Boso Peninsula | C | 4 |
| 7 | Who Is the Philosopher That Said "Cogito, Ergo Sum"? | A | Plato | B | Socrates | C | Kant | D | Descartes | D | 3 |
| | ... | | ... | | ... | | ... | | ... | | ... |

FIG.5

| Question | Confident | Unconfident | |
|---|---|---|---|
| | Incorrect | Correct | Incorrect |
| | Information of Answer Options | Information Concerning Correct Answer | Hint |
| 1 | A: Study the Distributive Law<br>B: Study the Distributive Law<br>C: Minus ×Plus =Minus | Factorize it as (x-y)(x-y),<br>and the Distributive Law Says<br>x^2-xy-xy+y^2=x^2-2xy+y^2. | (x-y)(x-y),Distributive Law |
| 2 | A: 3rd Shogun; Instituted Sankin-Kotai<br>B: 4th Shogun, Enforced Kanbunno-Chi<br>D: 6th Shogun, Abolished Shorui-Awaremino-Rei Orders | 5th Shogun; Ascribing His Loss of the Only Son to Killing Living Things, Enforced Shorui-Awaremino-Rei Order. | Called Inukubou |
| 3 | A: cash<br>B: bank<br>D: buy | Credit Means Trust.<br>Also Means Reputations, Works, and the Like. | A Credit Card Indicates ○○ |
| ... | ... | ... | ... |

FIG.6

| | | Correctness of Answer | |
|---|---|---|---|
| | | Correct | Incorrect |
| Confidence | Yes | Indicate ○ | Information of Answer Option<br>Hint |
| | No | Information of Correct Answer<br>Reason behind Correct Answer | Display Hint |

|  |  | Correctness of Answer | |
|---|---|---|---|
|  |  | Correct | Incorrect |
| Confidence | Yes | Understood | Mistake |
|  | No | Random Guess | Not Understood |

*FIG.11*

| Question No. | Status of User's Understanding | | |
|---|---|---|---|
| | 1st Time | 2nd Time | 3rd Time |
| 1 | Understood | Understood | – |
| 2 | Understood | – | – |
| 3 | Random Guess | Random Guess | Understood |
| 4 | Mistake | Understood | – |
| 5 | Understood | Understood | – |
| 6 | Not Understood | Random Guess | Understood |
| 7 | Random Guess | Understood | |
| ... | ... | ... | ... |

| | | Correctness of Answer | |
| --- | --- | --- | --- |
| | | Correct | Incorrect |
| Confidence | Yes | 0.1 | 3 |
| | No | 3 | 3 |

FIG. 15

| Manipulation Input | Help for Each Manipulation Input Button |
|---|---|
| Play Back | Allows You to View Recorded Programs and Stored Programs |
| Program Guide | Allows You to Confirm Programs to Be Broadcast |
| Dubbing | Duplicates Recorded Video Data to DVD or HDD |
| ... | ... |

(a) Example of Help Based on Manipulation Input Button

| Manipulation Input | Prospective Appliance Operation | | |
|---|---|---|---|
| | Candidate 1 | Candidate 2 | Candidate 3 |
| Play Back | Play Back Programs Stored in HDD | Play Back DVD | Play Back Still Pictures |
| Program Guide | List of Programs Scheduled to Be Broadcast | List of Recorded Programs | Search for Recommended Programs |
| Dubbing | Duplicate Video Data to DVD | Utilize DVD Data for HDD | Record Program |
| ... | ... | ... | ... |

(b) Example of Presenting Prospective Appliance Operations

Results of Disappointment Signal Measuring Experiment
(All Tests for 10 Test Subjects are Added)

Process a: Determination Using Threshold

Process b: Determination Using Mahalanobis Distances

INFORMATION PROCESSING SYSTEM, INFORMATION PROCESSING APPARATUS, AND METHOD

TECHNICAL FIELD

The present invention relates to a technique of providing information or services for a user. More specifically, the present invention relates to an appliance and method which utilizes a biological signal, e.g., electroencephalograms, of a user to select and provide appropriate information or services, and a computer program to be executed in such an appliance.

BACKGROUND ART

In recent years, study systems are being developed which present a question, receive an answer input by a user, and present a correctness evaluation. In a study system, it is necessary to precisely infer the degree of understanding of the user during the study, in order to improve the efficiency of studying. The reason is that, if the degree of understanding of the user can be precisely inferred, it becomes possible to present a question in accordance with the degree of understanding and appropriately adjust content to be fed back as to what sort of content should be output with respect to an answer.

In such a study system, the degree of confidence as to how confident a user was in making his or her answer is a piece of information which is important in inferring the degree of understanding of the user. Various techniques for measuring the degree of confidence have conventionally been studied.

For example, Patent Document 1 discloses a study system which, when a condition such as a question level is input, automatically selects an exercise. This study system measures the degree of confidence of a user by collecting a subjective evaluation of the user for each question, in the form of a questionnaire, during study. Then, based on the degree of confidence and the correctness of the answer, the study system infers the degree of understanding of the user, and selects and asks exercises in accordance with the degree of understanding of the user.

Patent Document 2 discloses a technique of inferring a user state based on biological information. In Patent Document 2, a user state when a difference has occurred between a user's anticipation of an appliance operation and an actual appliance operation is defined as a disappointment. Then, the appliance detects a disappointment state of the user, by using a disappointment signal component (positive component) which appears in an event-related potential as an index. A disappointment signal component appears in the case where, with respect to a confident manipulation, an appliance has failed to operate as expected. Thus, by using this signal it is possible to measure the degree of confidence with respect to a manipulation. Utilizing the characteristics of an event-related potential, this appliance detects a disappointment state of a user immediately (about 600 ms) after an answer input, and thus realizes a change of an interactive service.

[Patent Document 1] Pamphlet of International Laid-Open No. WO2003/050782

[Patent Document 2] Pamphlet of International Laid-Open No. WO2005/001677

DISCLOSURE OF INVENTION

Problems to be Solved by the Invention

In the study system described in Patent Document 1, it is indispensable for the user to answer a questionnaire, which is cumbersome because it hinders concentration on the task, thus bothering the user. Moreover, a subjective evaluation of a user's confidence will be susceptible to various factors, and may even allow for deception. Thus, there are possibilities that the degree of confidence of the user may not be correctly exhibited.

On the other hand, the appliance described in Patent Document 2 utilizes a disappointment signal component which appears about 600 ms after a point in time at which the appliance makes an output, and thus is only able to change a content which has already been output. In other words, this appliance is unable to adjust a content to be output at a point in time before the appearance of a disappointment signal component.

An objective of the present invention is to objectively evaluate a degree of confidence without permitting a user's subjective evaluation, and determine a content to be output based on this evaluation.

Means for Solving the Problems

An information processing system according to the present invention comprises: an input section for receiving an input from a user; a signal detection section for measuring a signal concerning an event-related potential of electroencephalograms of the user; a determination section for determining a degree of confidence of the user with respect to the input based on an amount of negative shift in the event-related potential during a predetermined period after the input is received; a control section for determining a content to be presented based on the degree of confidence; and an output section for presenting the determined content.

The output section may present a question to the user; as the input, the input section may receive an answer of the user to the question which is output by the output section; based on the degree of confidence, the control section may determine to present information related to the question or related to a correct answer thereto; and the output section may present the information after lapse of the predetermined period.

The determination section may determine the degree of confidence of the user by defining as the predetermined period a period within about 2000 milliseconds starting from a point in time of receiving the input.

The information processing system may further comprise a database storing information related to the question and related to the correct answer, wherein, the control section may determine correctness of the answer of the user by referring to the database, and based on the degree of confidence of the user and a determination result of correctness, select the information related to the question or related to the correct answer thereto.

The database may store information of a plurality of hints related to the correct answer; and the control section may select from among the hints based on the degree of confidence of the user and the determination result of correctness.

The control section may output information representing a degree of understanding of the user, based on the degree of confidence of the user and the determination result of correctness.

The amount of negative shift in the event-related potential may have a corresponding relationship with a gradient of a waveform of negative shift; and the determination section may retain a threshold which falls between a gradient value of negative shift corresponding to 'confident' and a gradient value of negative shift corresponding to 'unconfident', and by comparing a gradient of a waveform of the acquired event-related potential against the threshold, make a 'confident' determination if the gradient of the waveform is smaller than the threshold, and make an 'unconfident' determination if the gradient of the waveform is larger than the threshold, and output information representing the determination result to the control section.

The amount of negative shift in the event-related potential may have a corresponding relationship with a gradient of a waveform of negative shift; and the determination section may include a table which retains first numerical values representing a gradient of negative shift corresponding to 'confident' and second numerical values representing a gradient of negative shift corresponding to 'unconfident', the first numerical values and the second numerical values being previously acquired through an experiment, and based on a Mahalanobis distance between a gradient value of a waveform of the acquired event-related potential and the first numerical values and on a Mahalanobis distance between a gradient value of the waveform of the acquired event-related potential and the second numerical values, output information representing the determination result to the control section.

The information processing system may further comprise a database in which input content and explanations concerning functions of the information processing system are stored in association, wherein, in accordance with the degree of confidence, the control section may refer to the database and selects an explanation which is associated with the input from the user; and the output section may present the selected explanation after lapse of the predetermined period.

The determination section may determine presence or absence of confidence of the user with respect to the input by defining as the predetermined period a period within about 2000 milliseconds starting from a point in time of receiving the input.

The control section may refer to the database when the determination section determines that the user is unconfident.

A plurality of prospective explanations may be stored in association with each input content in the database; and the control section may select at least one of the plurality of prospective explanations.

Ordinal ranks may be set for the plurality of prospective explanations in the database; and the control section may select from among the plurality of prospective explanations in accordance with the ordinal ranks.

After the output section presents the explanation, the input section may further receive an input from the user; and the control section may instruct that a function be executed based on the further received input.

An information processing apparatus according to the present invention is connected to: an input device which receives an input from a user; an output device which presents information to the user; and a signal detection device which measures a signal concerning an event-related potential of electroencephalograms of the user. The information processing apparatus comprises: a determination section for determining a degree of confidence of the user with respect to the input based on an amount of negative shift in the event-related potential during a predetermined period after the input is received; a control section for determining a content to be presented to the user based on the degree of confidence, and transmitting the determined content to the output section after lapse of the predetermined period, wherein, the output section presents the content.

An information processing method according to the present invention comprises the steps of: receiving an input from a user; measuring a signal concerning an event-related potential of electroencephalograms of the user; determining a degree of confidence of the user with respect to the input based on an amount of negative shift in the event-related potential during a predetermined period after the input is received; determining a content to be presented to the user based on the degree of confidence; and presenting the determined content.

A computer program according to the present invention is executable on a computer, and is recordable on a storage medium. The computer program causes the computer to execute: a step of receiving an input from a user; a step of measuring a signal concerning an event-related potential of electroencephalograms of the user; a step of, based on an amount of negative shift in the event-related potential during a predetermined period after the input is received, determining a degree of confidence of the user with respect to the input; a step of determining a content to be presented to the user based on the degree of confidence; and a step of presenting the determined content.

Effects of the Invention

According to the present invention, based on an amount of negative shift in an event-related potential during a predetermined period after an answer is received, the degree of a user's confidence with respect to the answer is determined. Then, the content of an output is appropriately selected in accordance with the determined degree of confidence. Since the output is determined while considering the psychological state of the user, rather than being determined based only on the answer, the most appropriate output for each individual user can be provided.

For example, in a study system where a question is presented and a correctness evaluation is presented in response to an answer input of the user, the degree of the user's confidence with respect to the answer is automatically inferred, and the content of feedback can be changed in advance, in accordance with the inferred degree of confidence. In such a study system, in the case where unconfident answer is a correct answer, based on the degree of the user's confidence and the correctness of the answer, information concerning the correct answer, e.g., a detailed explanation for the question can be presented, instead of displaying a correctness evaluation of "◯". As a result, the efficiency of studying is drastically improved.

BRIEF DESCRIPTION OF DRAWINGS

FIG. 2 A diagram showing the functional block construction of the service providing system 5 according to the present embodiment.

FIG. 3 A diagram showing a table which stores values of gradients of negative shift concerning confident/unconfident, obtained through a preliminary investigation.

FIG. 4 A diagram showing specific examples of data concerning questions stored in a question DB 53.

FIG. 5 A diagram showing specific examples of hints stored in a hint DB 300.

FIG. 6 A diagram showing the contents of processes to be selected in accordance with the correctness of an answer and the degree of confidence.

FIG. 11 A diagram showing an example of a result table stored in a result-storing DB 400.

FIGS. 15 (a) and (b) show examples of help DBs 650 in the case where a confidence-detecting service providing apparatus 26 is a DVD recorder.

Figure 1:
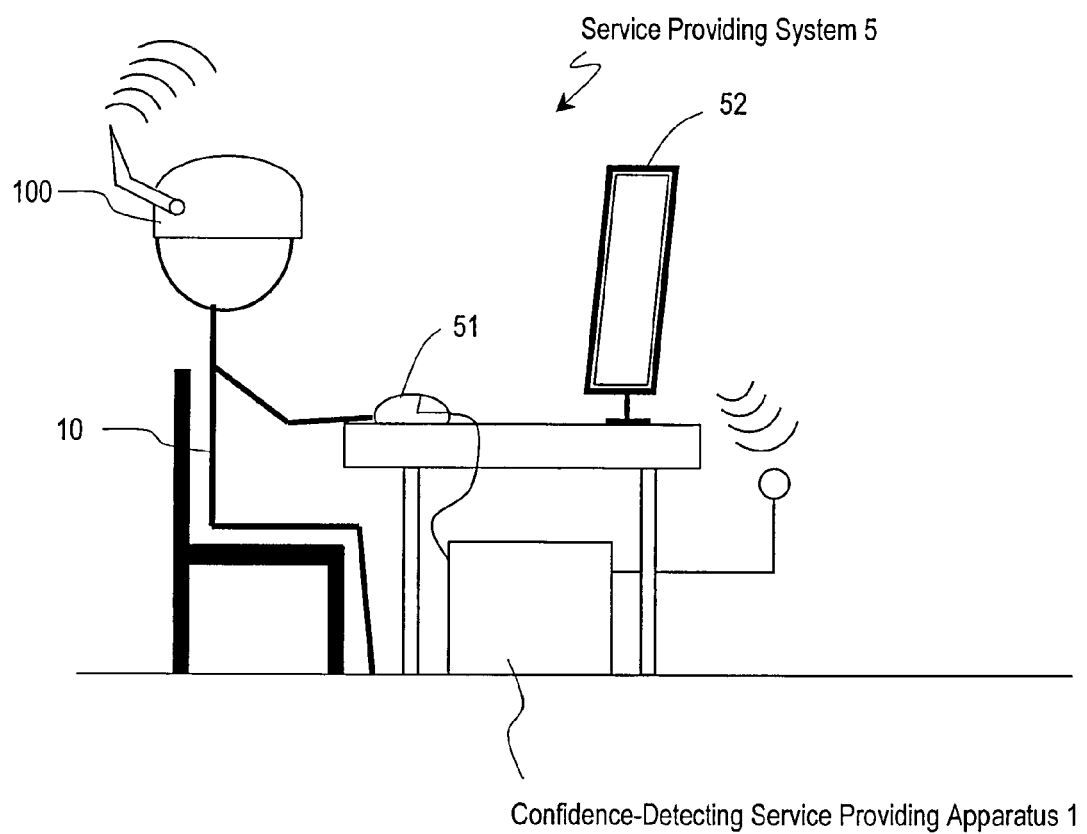
FIG. 1 A diagram showing an exemplary construction of a service providing system 5 according to the present embodiment.

DESCRIPTION OF THE REFERENCE NUMERALS 1, 2, 26 confidence-detecting service providing apparatus
3 RAM
4 computer program
5, 15, 25 service providing system
10 user
12 central processing unit (CPU)
50, 500, 600 appliance operation control section
51 input section (mouse)
52 output section (display)
53 question DB
100 biological signal detection section
200 user state determination section
300 hint DB
400 result-storing DB
650 help DB

BEST MODE FOR CARRYING OUT THE INVENTION

Hereinafter, with reference to the accompanying drawing, embodiments of information processing systems and information processing apparatuses according to the present invention will be described.

The inventors have found that the degree of a user's confidence to an answer appears in an SPN component (negative potential) of an event-related potential, in a time slot from the inputting of an answer to the displaying of a correctness evaluation. Specifically, the inventors have found that the degree of a user's confidence can be determined based on an amount of negative shift in the event-related potential during a predetermined period after receiving an answer.

The "event-related potential" (ERP) is a portion of the electroencephalograms, referring to a transient potential fluctuation in the brain which occurs in temporal relationship with an external or internal event. Its SPN component is an intrinsic component called SPN (Stimulus-Preceding Negativity), among the various waveform components composing the event-related potential. This intrinsic component is a slow negative potential which appears before an information-containing stimulation such as a feedback stimulation. To be more specific, unlike an evoked potential (which is passive and extrinsic) that relies on an external sensory stimulation, an intrinsic component is said to be an intrinsic potential which fluctuates so as to reflect the cognitive attitude (degree of motivation toward a task) of the test subject with respect to an external stimulation (event).

Hereinafter, with reference to FIG. 17 to FIG. 21, an event-related potential measuring experiment which was performed by the inventors will be described first, and it will be described how the degree of a user's confidence with respect to a question that has been asked appears in a waveform component of the event-related potential, during a period from the inputting of an answer to the displaying of a correctness evaluation. Thereafter, with reference to FIG. 1 to FIG. 21, embodiments of the present invention will be described.

1. Event-Related Potential Measuring Experiment

FIG. 17(a) is a diagram showing the outline of the experimental procedure. This experiment is composed of the following steps: a question is presented to a test subject (step A); looking at the question, the test subject manipulates an appliance while imaging an act which is believed to be necessary (step B); and the correctness of the manipulation result is fed back to the test subject (step C).

The following instruction was given to the test subject prior to the experiment. "A question and four options will be simultaneously displayed on the display. There is no time limit for answering, so please take your time. Next, you will write your degree of confidence on a separate piece of paper. After thinking, please check an option which you think is absolutely incorrect, and choose your degree of confidence with respect to the question, from among Absolutely Correct, Probably Correct, Probably Incorrect, or Absolutely Incorrect. Options A to D for the question correspond to A to D on the keyboard. When you finish writing your degree of confidence, place your finger on the key with which you are going to make an answer, and move your gaze to the fixation point on the display. Take one breath, and then press your key while watching the fixation point, without moving your eyes. In 2 seconds after you pressed the key, a result as to whether the answer is correct or not will be indicated by ○ or X The ○/X result will be displayed for 2 seconds. All this while, please keep your gaze unmoved from the fixation point. A next question will be displayed in 2 seconds after the ○/X indication disappears. This will be similarly repeated down to 60 questions."

Next, the specific experimental procedure will be described. FIG. 17(b) is a flowchart showing a procedure corresponding to one test. A question and four options are presented on the screen (S1101). Looking at the presentation, the test subject considers which option is the correct option, writes his or her degree of confidence on a separate piece of paper (S1102), and determines a corresponding keyboard and presses the key (S1103). From a starting point defined as the timing with which the test subject's answer is input, an event-related potential in the electroencephalograms of the test subject is measured (S1104). In 2000 milliseconds (ms) after the inputting of the test subject's answer (S1105), "○" "X" or is indicated based on whether the test subject's answer was correct or not (S1106). The event-related potential since the test subject's answer is input and until the result of correctness is fed back is processed to determine the degree of confidence of the test subject (S1107).

Figure 18:
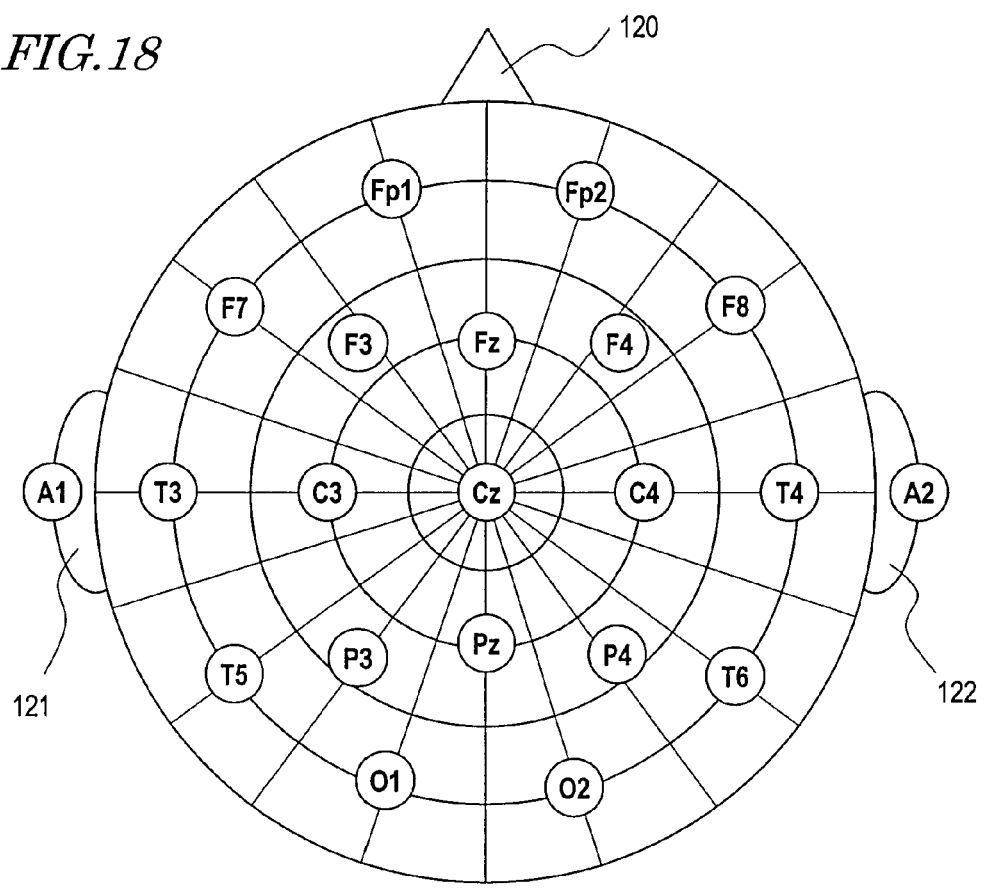
FIG. 18 A diagram showing positions at which electrodes for measuring electroencephalograms of a test subject are attached.

FIG. 18 shows positions at which electrodes for measuring the electroencephalograms of a test subject are attached. These attachment positions comply with the International 10-20 system. As an aid for clarifying the positional relationship, a nose 120, a left ear 121, and a right ear 122 of the test subject are shown in FIG. 18. In FIG. 18, any electrode that is on a median line which is equidistant from the left ear 121 and the right ear 122 and passes through the nose 120 is labeled as "z".

The electrodes for measuring the event-related potential were attached at 1) Fz: median forehead, 2) Cz: median center, 3) Pz: median vertex, 4) EOG: above the right eye, 5) 6) A1,A2: both earlobes, 7) body ground, and (Z): root of nose. The sampling frequency was 200 Hz, and the band-pass filter was 0.16 to 20 Hz.

In the analysis of the experimental data, a 0.05 to 10 Hz band-pass filter was used, and a waveform from 200 ms to 0 ms before the answer input was used for baseline correction. Moreover, in the present experiment, in order to eliminate noises associated with blinks, an electrooculogram (EOG) was simultaneously measured, and any test resulting in an EOG component having an amplitude of 100 μV or more was excluded from the arithmetic for fear of electroocular noise being mixed.

Figure 19:
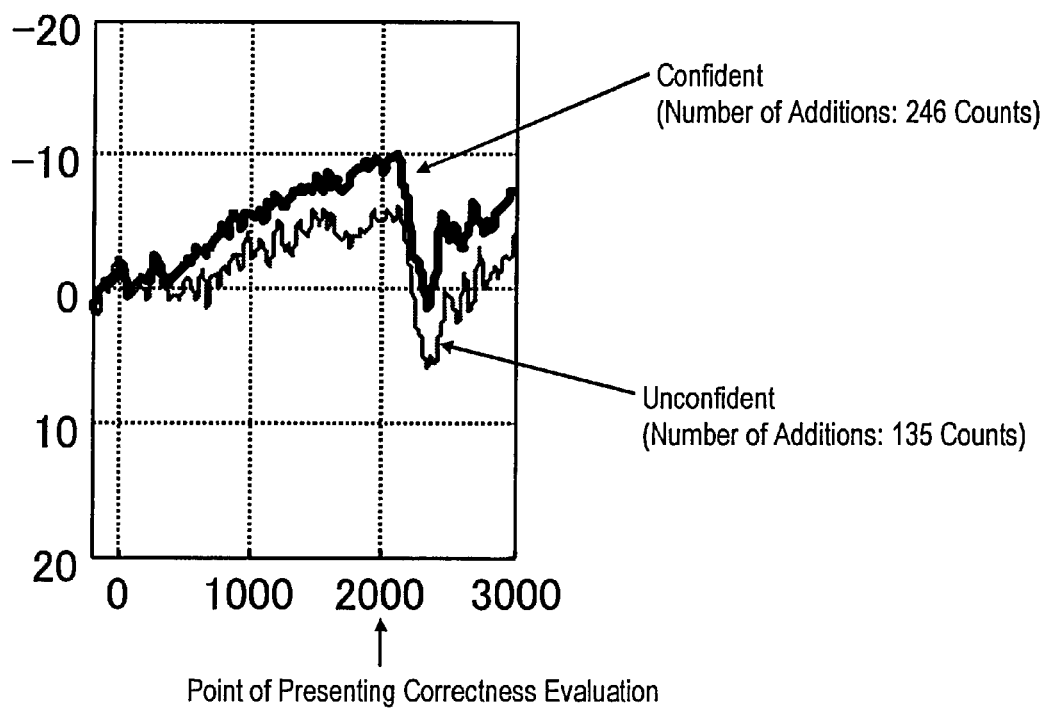
FIG. 19 A graph showing waveforms of event-related potentials, obtained by taking total arithmetic means of experimental data of ten test subjects, where the starting point is an inputting of an answer.

FIG. 19 is a graph showing waveforms of event-related potentials, obtained by taking total arithmetic means of experimental data of ten test subjects, where the starting point is an inputting of an answer. The horizontal axis of the graph represents time from the answer input, in units of ms. The answer input is made at 0 ms, and the correctness evaluation is presented at 2000 ms. The vertical axis of the graph represents potential in units of μV. Note that the vertical axis of the graph is indicated so as to read minus in the upper direction and plus in the lower direction.

The two waveforms shown in the graph of FIG. 19 are obtained by, based on the degree of confidence written on the separate piece of paper, separately taking total arithmetic means of Absolutely Correct, shown as "Confident", and of Absolutely Incorrect, shown as "Unconfident". The thick line shows the waveform of "Confident", i.e., where the user has answered with confidence. The thin line shows the waveform of "Unconfident", i.e., where the user has not been able to answer with confidence. The numbers of additions made were 246 and 135, respectively.

In a time slot from the point of answer input (0 ms) to the point of feeding back the result of correctness (2000 ms), both waveforms gently shift toward negative. In other words, these waveforms are the waveforms showing an SPN component.

It is also seen that, as compared to the "Unconfident" waveform, the SPN component of the "Confident" waveform shown in FIG. 19 has a greater amount of shift toward negative since the answer input and until the presentation of the correctness evaluation. This justifies the concept of being able to detect the degree of the user's confidence by measuring the amount of shift of the SPN component toward negative.

Note that it has been known that, in a time evaluation task where a feedback is given as to whether a pressing of a button by the test subject corresponds to a designated number of seconds, or in a gambling task where a bet is made as to whether one can get a reward or not, an SPN component appears as a gentle negative shift in a time slot since the act is done and until the result is fed back, and the negative shift increases in amplitude when the pecuniary reward satisfies certain conditions (for example, see the following paper: "Information or Emotion?—Influences of Amount of Information and Rewards on Stimulus-Preceding Negativity (SPN)" (*Seirishinrigaku to Seishinseirigaku* (or *Japanese Journal of Physiological Psychology and Psychophysiology*) Vol. 19, No. 3. 2001)).

However, the degree of confidence as to an act is generally unclear under the experiment conditions of a time evaluation task or gambling task. Therefore, it has so far been quite unknown as to how the SPN component changes with the degree of confidence, and there has not even been a concept of trying to find a relationship therebetween.

As has been made clear by this experiment, depending on the degree of confidence of the test subject with respect to a question, there is a clear difference in the SPN component of an event-related potential that is measured with an electroencephalograph. Therefore, this event-related potential can be used as a "degree of confidence" in the determination of a user state. It can be said that, based on a very novel concept, the inventors have made a finding that the SPN component varies with the degree of confidence.

2. Distinction of Waveforms of Event-Related Potentials

Now, a method of determining the degree of confidence of a user with respect to an answer based on the waveform of an event-related potential will be described. Since the amplitude of an event-related potential is as small as ⅒ of that of the background electroencephalograms, it is said to be difficult to distinguish with a simple technique of subjecting the potential waveform to threshold processing or the like. On the other hand, as shown in FIG. 19, the waveform of an event-related potential showing the degree of confidence has been observed to shift toward negative continuously and gently, for a relatively long time until the result of correctness is presented. Therefore, it is considered that the degree of confidence can be determined by using as an index the amount(s) of negative shift at one or more specific points.

However, as can be easily seen from its waveform, a linear approximation of the waveform of an event-related potential is possible during a period since the user inputs an answer and until the result of correctness is presented. Moreover, because the amount of negative shift and the gradient of the approximation line are in proportional relationship, the degree of confidence will be determined by utilizing the gradient of the waveform toward negative (gradient of negative shift) in the following.

Figure 20:
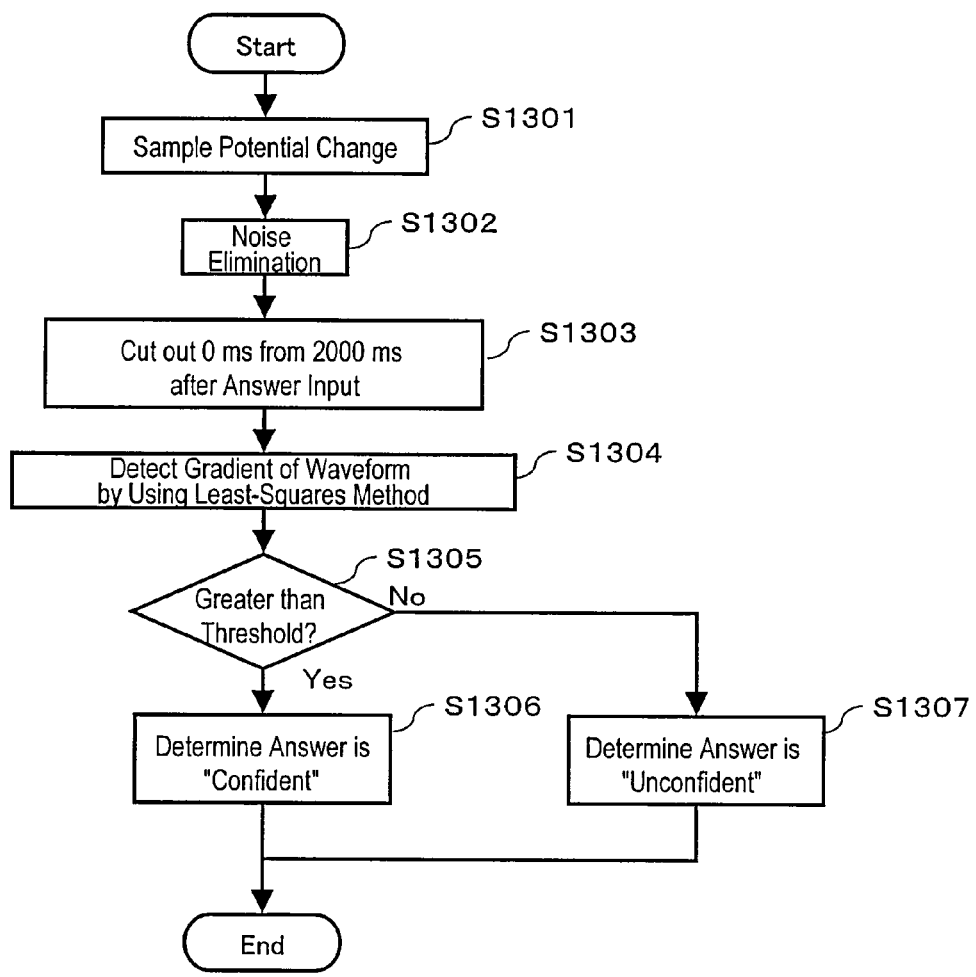
FIG. 20 A flowchart showing a procedure of distinguishing the degree of confidence by subjecting a gradient of negative shift to threshold processing.

The flowchart of FIG. 20 shows a procedure of distinguishing the degree of confidence by subjecting a gradient of negative shift to threshold processing (process a). Hereinafter, the steps of process a will be described in order. Note that, as is clear from the fact that it is shown as a flowchart, this distinction process indicates a computer program-based processing procedure. This computer program is stored in an apparatus such as that shown in FIG. 2, and executed by a central processing unit (CPU) of that apparatus. The details of such an apparatus and an information processing system comprising the apparatus will be specifically described later.

First, starting at the timing of an answer input, a potential change of the electroencephalograms is sampled (S1301). Examples of sampling frequencies are 200 Hz, 500 Hz, and 1000 Hz.

Next, noise is eliminated from the waveform of the potential change that has been sampled (S1302). For example, the signal is allowed to pass through a 0.16-20 Hz band-pass filter in order to cut off the low-frequency and high-frequency components which are mixed in the signal. Moreover, any waveform whose EOG has an amplitude of 100 μV or more is discarded from the subject of distinction, thus reducing the influences of blinks and ocular motions.

Next, out of the potential change of the electroencephalograms from which noise has been eliminated, the waveform of a region that relates to the detection of the degree of confidence of an answer is cut out (S1303). From the aforementioned experimental results, it is known that the degree of confidence for an answer is detectable in a time slot from 0 ms after an answer input to the feeding back of an evaluation (i.e., 2000 ms in the aforementioned experiment). Therefore, 0 ms to 2000 ms after an answer input may be cut out, for example. As will be appreciated, the range to be cut out is not limited to the above, since the degree of confidence appears as a difference in the waveform immediately after the answer input as shown in FIG. 19. Any time slot until a feedback is presented, e.g., 200 ms to 700 ms or 300 ms to 1500 ms after an answer input, may be set.

Next, the gradient of negative shift of the signal is calculated (S1304). The commonly-used least-squares method may be used for the calculation of the gradient. For example, equation 1 shows a calculation formula for the linear gradient in the case where a linear approximation of the waveform is performed.

$$a = \frac{(\overline{xy} - \overline{x} * \overline{y})}{(\overline{x^2} - \overline{x}^2)} \quad \text{[equation 1]}$$

In equation 1, a is a gradient of negative shift of potential which is to be obtained; and x and y are, respectively, data of sampling time for the waveform that has been cut out and a potential value for each sampling. Any overline indicates an average value.

Then, the gradient of negative shift of the signal is compared against a threshold (S1305). In the aforementioned experiment, a threshold of −0.004 was derived by averaging the average values of the respective gradients of confident/unconfident negative shift of the ten test subjects. When determining a threshold in practice, a preliminary investigation may be performed in advance, and average values of the respective gradients of confident/unconfident negative shift of the users (pupils) may be obtained. The method of determining a threshold is not limited thereto; for example, it may be set by assigning a weight to either one of confident/unconfident. It will be appreciated that a threshold may also be determined for each individual user.

If the gradient of negative shift of the signal is smaller than the threshold (Yes from S1305), it is determined that the user has answered the question with confidence (S1306). On the other hand, if the gradient is greater than the threshold (No from S1305), it is determined that the user has answered the question without confidence (S1307). Note that the event-related potential in the time slot from the answer input to the feeding back of the result undergoes a gentle negative shift. Therefore, the gradient takes a minus value, and being smaller than the threshold means an increased amount of negative shift.

In the case of using process a, the confident/unconfident distinction ratio was 55%. This indicates a possibility of being able to determine the degree of confidence in a situation where the event-related potential has such a low S/N that it makes each test distinction difficult, and the confident and unconfident waveforms are similar in trends because they both shift toward negative starting from the answer input, which makes determination even more difficult. Moreover, while the overall distinction ratio was 55%, the ratio of wrongly determining unconfident to be confident, which would be a crucially wrong determination in studying situations, was about 15%. Therefore, the degree of confidence determination using process a, which subjects the gradient of negative shift to threshold processing, is usable for studying situations.

However, in order to allow the degree of confidence to be determined with an even high precision, not only the gradient of negative shift is simply subjected to threshold processing, but confident/unconfident groups are previously defined from the test-to-test gradients of confident/unconfident negative shift of all test subjects, and a determination is made based on a discrimination ratio using Mahalanobis distances. A Mahalanobis distance indicates a distance from the center of gravity of a group, by taking into consideration the variance and covariance of data. A determination using the Mahalanobis distance is known to provide a higher distinction ability than making a determination through simple threshold processing. Equation 2 below shows a calculation formula for a Mahalanobis distance.

$$D_1^2(x_1, x_2) = (x_1 - x_1^{(1)} \quad x_2 - x_2^{(1)}) \begin{bmatrix} s_{11}^{(1)} & s_{12}^{(1)} \\ s_{21}^{(1)} & s_{22}^{(1)} \end{bmatrix}^{-1} \begin{bmatrix} x_1 - x_1^{(1)} \\ x_2 - x_2^{(1)} \end{bmatrix} \quad \text{[equation 2]}$$

$$D_2^2(x_1, x_2) = (x_1 - x_1^{(2)} \quad x_2 - x_2^{(2)}) \begin{bmatrix} s_{11}^{(2)} & s_{12}^{(2)} \\ s_{21}^{(2)} & s_{22}^{(2)} \end{bmatrix}^{-1} \begin{bmatrix} x_1 - x_1^{(2)} \\ x_2 - x_2^{(2)} \end{bmatrix}$$

In formula 2, $D_1^2$ is the square of a Mahalanobis distance between the gradient of negative shift of a measured potential and the unconfident group; $x_1$ (gradient of negative shift when unconfident); $x_2$ (gradient of negative shift when confident); $x_1^{(1)}$ (average value of gradients of negative shift of the unconfident group when unconfident); $x_2^{(1)}$ (average value of gradients of negative shift of the unconfident group and the confident group); and s (variance/covariance matrix of the unconfident group). Similarly, $D_2^2$ (the square of the Mahalanobis distance from the confident group) is obtained.

Figure 21:
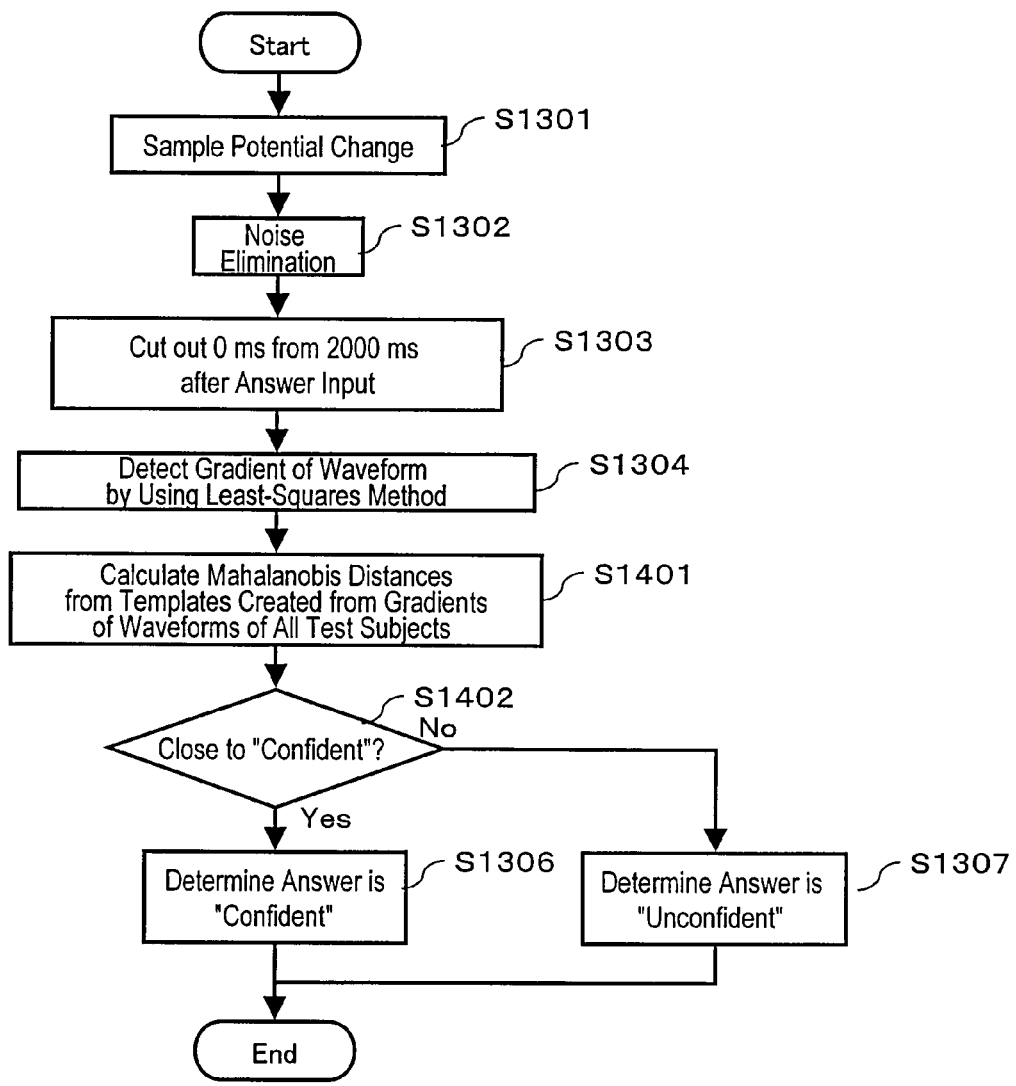
FIG. 21 A flowchart showing a procedure of distinguishing the degree of confidence based on a Mahalanobis distance.

The flowchart of FIG. 21 shows a procedure of distinguishing the degree of confidence based on Mahalanobis distances (process b). This process is also realized as a processing procedure which is based on a computer program, similarly to the flowchart of FIG. 20. Any step where the same process as in FIG. 20 is performed is denoted by the same numeral, and the description thereof is omitted.

First, step S1301 to step S1304 are the same as the processes in FIG. 20.

Next, from the respective gradients of confident/unconfident negative shift of all of the test subjects, Mahalanobis distances between previously-created templates and the gradient of negative shift from each test are calculated (S1401). From the calculated Mahalanobis distances, it is determined as to which one of the confident and confident templates the signal waveform is closer to (S1402).

The confident/unconfident distinction ratio according to process b was 62%, showing a further 7% improvement over process a. As has also been mentioned with regard to process a, this distinction ratio is sufficiently usable in studying situations. Thus, it has been shown that, also according to this process b, confident/unconfident with respect to an answer are distinguishable from the event-related potential in the time slot from the answer input to the feeding back of the result.

Moreover, instead of a distinction using the gradient of negative shift, or in addition to making a distinction using the gradient of negative shift, other techniques may also be employed. For example, as described in Patent Document 1, templates for the respective signal components of confident/unconfident may be created with respect to each individual test subject, and determination may be made by using Mahalanobis distances from the created templates. Moreover, it would also be possible to make a determination based on the minimum value of amplitude of a signal component in the time slot from the answer input to the feedback.

3. System Construction of an Embodiment of the Present Invention

Hereinafter, an embodiment of the information processing apparatus and system according to the present invention will be described. The system and apparatus of the present embodiment utilizes an SPN component of an event-related potential of user electroencephalograms to automatically infer the degree of the user's confidence with respect to an answer. This inference is made after the user has input an answer, and before a result or the like is output to the user. The system and apparatus present to the user a content which is in accordance with the inferred degree of confidence.

Since the content of the information which is first presented is already suitable to each individual user, the user is much less often exposed to a presentation of disappointing information. Thus, the user is always able to receive a service which is suitable to himself or herself. Hereinafter, such an information processing system will be referred to as a "service providing system".

First, with reference to FIG. 1, a specific example of the service providing system will be described. With reference to FIG. 2 to FIG. 8, the general construction and operation of the service providing system will be described.

FIG. 1 shows an exemplary construction of the service providing system 5 according to the present embodiment. The service providing system 5 includes a confidence-detecting service providing apparatus 1 (hereinafter referred to as the "service providing apparatus 1"), a mouse 51, a display 52, and a biological signal detection section 100.

Now, an example will be described where the service providing system 5 is constructed as a study system. A "study system" is a system in which the service providing apparatus 1 presents a question to the user 10, and upon receiving an answer from the user 10, feeds back a correctness evaluation or the like to the user.

When the service providing apparatus 1 outputs a question on the display 52, the user 10 manipulates the mouse 51 to input an answer to the question that has been output.

Upon receiving the answer, the service providing apparatus 1 acquires a signal (brain-wave signal) which represents an event-related potential of the electroencephalograms of the user that is measured by the biological signal detection section 100. The biological signal detection section 100 according to the present embodiment is contemplated as a head-mount type electroencephalograph, and is capable of wirelessly transmitting a detected brain-wave signal to the service providing apparatus 1. This electroencephalograph has electrodes placed thereon, such that, when worn on the head of the user 10, the electrodes will come in contact with predetermined positions on the head.

In the case where an electrode placement similar to the conditions of the experiment described with reference to FIG. 17 to FIG. 21 is adopted, the electrodes are placed at Pz (median parietal), A1,A2 (both earlobes), and the nasion of the user 10, as shown in FIG. 18. However, it suffices if there are at least two electrodes, and potential measurements can be made with Pz and A1 alone, for example. The electrode positions are to be determined in terms of reliability of signal measurement, ease of wearing, and the like. As a result, the biological signal detection section 15 is able to measure an event-related potential of the user 10.

Based on the amount of negative shift in the event-related potential within a predetermined period after receiving the answer, e.g., within a period of 2000 ms from the answer input as a starting point, the service providing apparatus 1 determines presence or absence of confidence of the user 10 with respect to the answer. Note that this "predetermined period" is meant as before providing a correctness evaluation feedback for the user 10.

Then, based on the presence or absence of confidence, information related to the question or answer is selected, e.g., correctness of the answer or a hint. The service providing apparatus 1 displays the selected information on the display 52. The timing of displaying comes after the lapse of the aforementioned predetermined period. No earlier than at this point in time will the user be provided with some sort of information regarding the answer.

As a result of the above-described processing, after inputting an answer, the user 10 will receive a presentation of only a result of correctness when being confident; receive a presentation of a hint concerning the question when being unconfident and having made the wrong answer; or receive a presentation of solutions to the question, etc., even when having made the correct answer. Thus, an efficient study can be realized.

4. Detailed Construction of the System According to Embodiment 1

FIG. 2 shows a functional block construction of the service providing system 5 according to the present embodiment. FIG. 2 also shows detailed functional blocks of the service providing apparatus 1. The user block 10 is shown for convenience of description.

The service providing apparatus 1 is connected to the input section 51, the output section 52, and the biological signal detection section 100 in a wired or wireless manner, and performs transmission and reception of signals. Although FIG. 2 illustrates the input section 51, the output section 52, and the biological signal detection section 100 as separate entities from the service providing apparatus 1, this is only exemplary. Some or all of the input section 51, the output section 52, and the biological signal detection section 100 may be provided within the service providing apparatus 1.

The input section 51 receives instructions from the user 10 to the service providing apparatus 1 as well as an answer to a presented question. The input section 51 corresponds to the mouse in FIG. 1, but may also include a keyboard, a voice input device, or the like. The output section 52 is a device which receives a signal from the service providing apparatus 1, and displays a content based on that signal, e.g., a question to the user 10, a determination result of correctness, or a hint. The output section 52 corresponds to the display of FIG. 1, but may also include loudspeakers and the like.

The biological signal detection section 100 is an electroencephalograph which detects a biological signal from the user 10, and measures electroencephalograms as a biological signal. The user 10 is wearing the electroencephalograph in advance. The measure electroencephalograms of the user 10 are sampled so as to become computer-processable, and are sent to a user state determination section 200.

Next, the detailed construction of the service providing apparatus 1 will be described.

The service providing apparatus 1 is implemented as a computer system which executes the subsequently-described processes. The service providing apparatus 1 includes a RAM 3, a computer program 4, a central processing unit (CPU) 12, a question database (question DB) 53, and a hint database (hint DB) 300.

By executing the computer program 4 stored in the RAM 3, the CPU 12 realizes functions in accordance with the processing procedure of the program. In the present embodiment, the CPU 12 operates as the appliance operation control section 50 and the user state determination section 200.

The computer program to be utilized may be a single program, or may be two or more different programs. The computer program is in the form of a product which is recorded on a storage medium such as a CD-ROM and distributed on the market, or transmitted through telecommunications lines, e.g., the Internet. Note that the appliance operation control section 50 and the user state determination section 200 may also be realized by hardware means, e.g., a DSP, that comprises semiconductor circuitry in which a computer program is incorporated.

The appliance operation control section 50 has the following functions:
(1) a function of determining and outputting a question to be presented by referring to a question DB 53;
(2) a function of, upon receiving an answer input of the user 10 from the input section 51, determining the correctness of the answer based on the question DB 53; and
(3) a function of, based on the information of the degree of the user's confidence as determined by the user state determination section 200, determining and outputting the content of feedback by referring to the hint DB 300. Detailed descriptions concerning these functions will be provided after describing the question DB 53 and the hint DB 300.

On the other hand, the user state determination section 200 has the function of determining the degree of confidence of the user 10 from the event-related potential of the electroencephalograms.

Various methods for determining the degree of confidence may be possible. For example, the user state determination section 200 may use the gradient of negative shift as an index, and compare it against a predetermined threshold. If the gradient of negative shift is smaller than the threshold, a 'confident' determination is made, and if it is greater than the threshold, an 'unconfident' determination is made.

As this threshold, −0.004, which is calculated from the event-related potential measuring experiment in the above-described studying situation, can be used. Alternatively, a preliminary investigation may be performed in advance in order to measure the event-related potential during study, and an average value of the gradients of confident/unconfident negative shift of the users (pupils) may be used, or it may be calculated by obtaining the gradients of negative shift for each individual. In order to calibrate the gradients of negative shift, a generally very easy question (e.g., arithmetic calculation of one digit+one digit) and a generally very difficult question (e.g., cryptanalysis without example problems) may be incorporated into the study questions as appropriate, and a threshold may be determined by using them as the confident and unconfident gradients of negative shift, respectively, or the determined threshold may be learned by the system such that the threshold is updated as appropriate. Either threshold will be a numerical value between values of confident gradients of negative shift and values of unconfident gradients of negative shift. The threshold is retained in the user state determination section 200, for example.

As still another determination method, the user state determination section 200 may make the confident/unconfident determination by calculating Mahalanobis distances. In the case where this determination method is adopted, a table to serve as a reference is utilized. For example, FIG. 3 shows a table storing values of gradients of negative shift concerning confident/unconfident, which is obtained through a preliminary investigation. This table is retained in the user state determination section 200. In the table, for each test, values corresponding to 'confident' and values corresponding to 'unconfident' are classified as a confident group and an unconfident group, respectively.

Having obtained the value of a gradient of negative shift from an event-related potential of the user 10, the user state determination section 200 calculates a Mahalanobis distance a between that gradient value and the values of the confident group in the table, as well as a Mahalanobis distance b between that gradient value and the values of the unconfident group in the table. Mahalanobis distances can be derived from the calculation formula shown as equation 2. Between the Mahalanobis distances a and b, if a is smaller, a 'confident' determination is made; and if b is smaller, an 'unconfident' determination is made.

The question DB 53 and the hint DB 300 are databases which are constructed on a hard disk drive, for example. There may be one such hard disk drive, or a plurality of such hard disk drives.

The question DB 53 stores data concerning questions, e.g., questions, correct answers, and importance levels of the questions. FIG. 4 shows specific examples of data concerning questions stored in the question DB 53. In the "question" column, a question is shown after each question number, then followed by four sets of alphabetical letters as option names and contents of the options.

The hint DB 300 stores various information concerning hints and the like corresponding to the question DB 53. FIG. 5 shows specific examples of hints which are stored in the hint DB 300. The contents are generally divided in relation to the presence or absence of confidence. Stored are the followings: information corresponding to each answer option, which is adopted when 'confident' and 'incorrect'; information showing an explanation for arriving at the correct answer, which is adopted when 'unconfident' and 'correct'; and information concerning a hint, which is selected when 'unconfident' and 'incorrect'.

Now, the above operation of the appliance operation control section 50 will be specifically described.

By referring to the question DB 53, the appliance operation control section 50 determines a question to be next presented. Moreover, based on the degree of the user's confidence as determined by the user state determination section 200 and on the correctness of the answer as determined in response to an answer input of the user 10 from the input section 51, the appliance operation control section 50 changes the content of the feedback, based on the table shown in FIG. 6, for example.

Hereinafter, a specific description will be given with reference to FIG. 6. FIG. 6 shows the contents of processes to be selected in accordance with the correctness of an answer and the degree of confidence. Now, it is assumed that the answer of the user 10 with respect to question 2 in FIG. 4 was option A, which is incorrect.

In this case, if the determined degree of confidence of the user 10 shows "Confident", it is 'incorrect' and 'confident', and therefore the appliance operation control section 50 selects the process of presenting the "information of answer options" based on FIG. 6. Referring to the hint DB 300, the appliance operation control section 50 presents information concerning option A (which has been answered by the user 10), e.g., "A: 3rd Shogun; Enforced Sankinkotai" as described in the "information of answer options" column of FIG. 5.

If the degree of confidence of the user 10 is "Unconfident", it is 'incorrect' and 'unconfident', and therefore the appliance operation control section 50 selects the process to "display hint", based on FIG. 6. Referring to the hint DB 300, the appliance operation control section 50 presents the hint "Called Inukubou", as described in the "hint" column of FIG. 5.

Now assume that the answer of the user 10 to question 2 in FIG. 4 was option C, which is correct. In this case, if the determined degree of confidence of the user 10 is "Unconfident", it is 'correct' and 'unconfident', and therefore the appliance operation control section 50 selects the process of presenting "information of correct answer" or "reason behind correct answer", based on FIG. 6. Referring to the hint DB 300, the appliance operation control section 50 presents "5th Shogun; Ascribing his loss of the only son to . . ." as described in the "information concerning correct answer" column of FIG. 5.

Finally, if the degree of confidence of the user 10 is 'confident', it is 'correct' and 'confident', and therefore the appliance operation control section 50 displays the correctness evaluation result "○" based on FIG. 6.

5. Processes in the Service Providing System According to Embodiment 1

Next, with reference to the flowchart of FIG. 7, the overall flow of processes performed in the service providing system 5 of FIG. 2 will be described.

Figure 7:
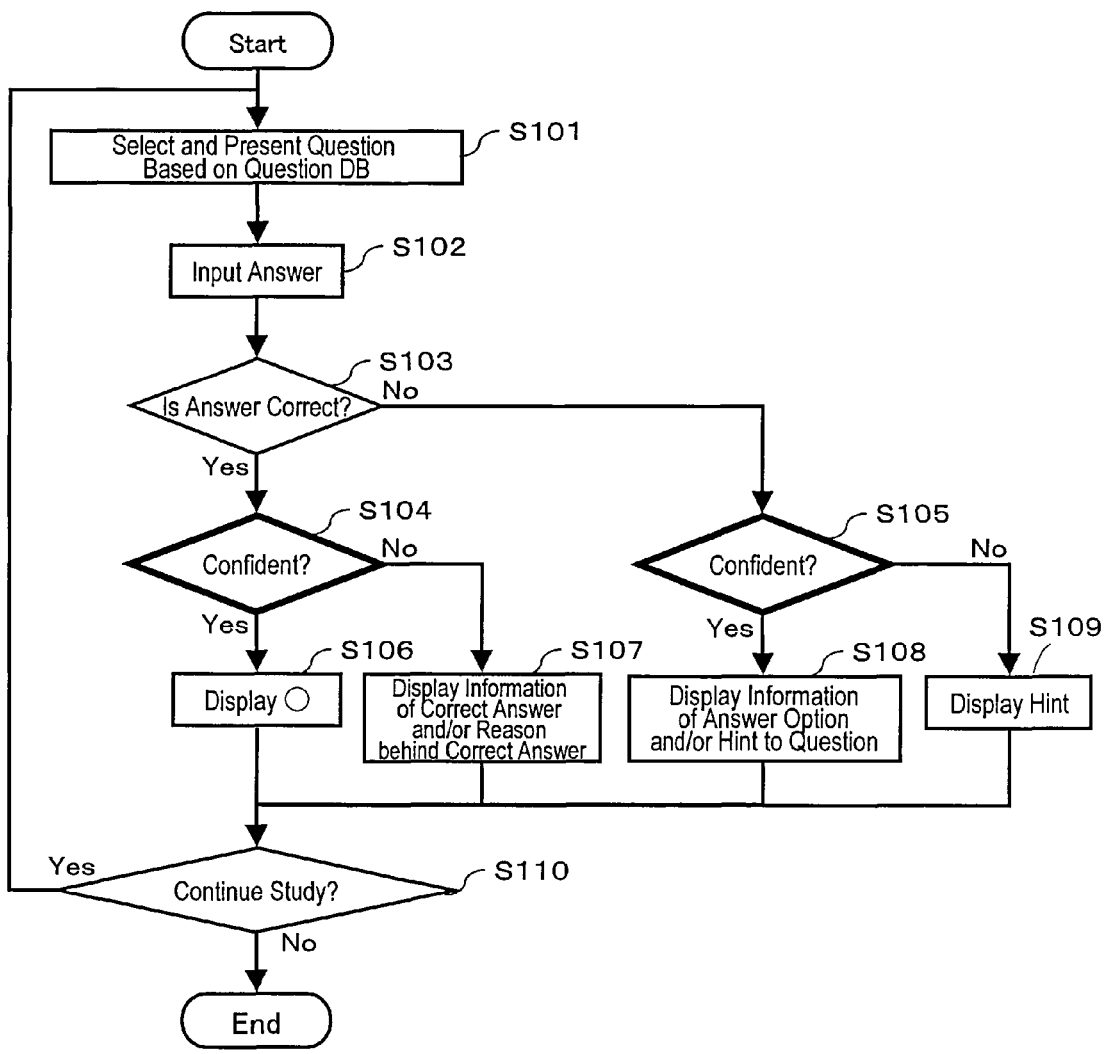
FIG. 7 A flowchart showing a procedure of processes by the service providing system 5.

FIG. 7 shows a procedure of processes by the service providing system 5.

At step S101, the appliance operation control section 50 first selects a question to be asked next from among the questions stored in the question DB 53, and sends the selected question to the output section 52. The output section 52 presents its content. The criterion for selecting the question may be, as shown in FIG. 4 for example, descending order of importance levels concerning the questions stored in the question DB 53.

At the next step S102, the user 10 answers the question presented at step S101. This answer is input via the input section 51 to the appliance operation control section 50. Inputting of the answer serves as a trigger when the user state determination section 200 acquires a necessary event-related potential.

At the following step S103, the appliance operation control section 50 compares the answer which is received at the input section 51 against a correct answer to the question which is stored in the question DB 53, and determines the correctness of the user's answer. If the answer is correct, control proceeds to step S104; if it is incorrect, control proceeds to step S105.

At step S104, using the timing of the answer input received at the input section 51 as the starting point, the user state determination section 200 acquires an event-related potential, and determines the degree of confidence of the user 10 with respect to the answer (presence or absence of confidence).

The user state determination section 200 outputs the determination result to the appliance operation control section 50. A similar process is performed also at step S105.

At step S104, if a 'confident' determination is made, control proceeds to step S106; and if an 'unconfident' determination is made, control proceeds to step S107. Similarly at step S105, the user state determination section 200 determines the degree of confidence and outputs a determination result. If 'confident', control proceeds to step S108; and if 'unconfident', control proceeds to step S109.

All of step S106 to step S109 executed next to the determination are processes where the appliance operation control section 50 selects the content of feedback to the user based on the answer and the degree of confidence of the user 10, and outputs it via the output section 52.

What is important with the outputting of this feedback content is its timing. Specifically, as can be seen from the waveform of FIG. 19, in order to determine the degree of confidence from an event-related potential, it is necessary to observe a time lag of about 1000 ms from the answer input at step S102 until the output of the feedback content at steps S106 to S109. In other words, within a period of about 1000 ms from the answer input, the service providing apparatus 1 acquires an event-related potential, determines the presence or absence of confidence, and selects the content for feedback. Then, after the lapse of the period, the content of the selected information is output to the user.

Note that the adjustment of output timing may be handled by the appliance operation control section 50 or by the output section 52. For example, if the appliance operation control section 50 operates so as to output information to the output section 52 after the lapse of the aforementioned period, the user will confirm the feedback content always after the lapse of the aforementioned period, so that the aforementioned output timing will be observed.

Hereinafter, the processes from step S106 to step S109 will be described. At step S106, via the output section 52, the appliance operation control section 50 displays only the result of correctness evaluation, i.e., "○", which means correct. At step S107, referring to the hint DB 103, the appliance operation control section 50 displays information of the correct answer or the reason behind the correct answer, via the output section 52. As a result, the user who has made the correct answer but was unconfident with the answer can know the reason why that answer is the correct answer.

On the other hand, at step S108, referring to the hint DB 103, the appliance operation control section 50 displays information of the answer option or a hint to the question, via the output section 52. At step S109, referring to the hint DB 103, the appliance operation control section 50 displays a hint to the question. The user having seen the content displayed at step S108 or step S109 can know that the answer was incorrect and also why the selected answer is incorrect although he or she was confident with it, and obtain a clue for arriving at the correct answer. These can be considered as hints related to the correct answer.

At step S110, the input section 51 receives an instruction from the user as to whether or not to continue the study. If the study is continued, control returns to step S101; and if the study is aborted, the process ends.

Figure 8:
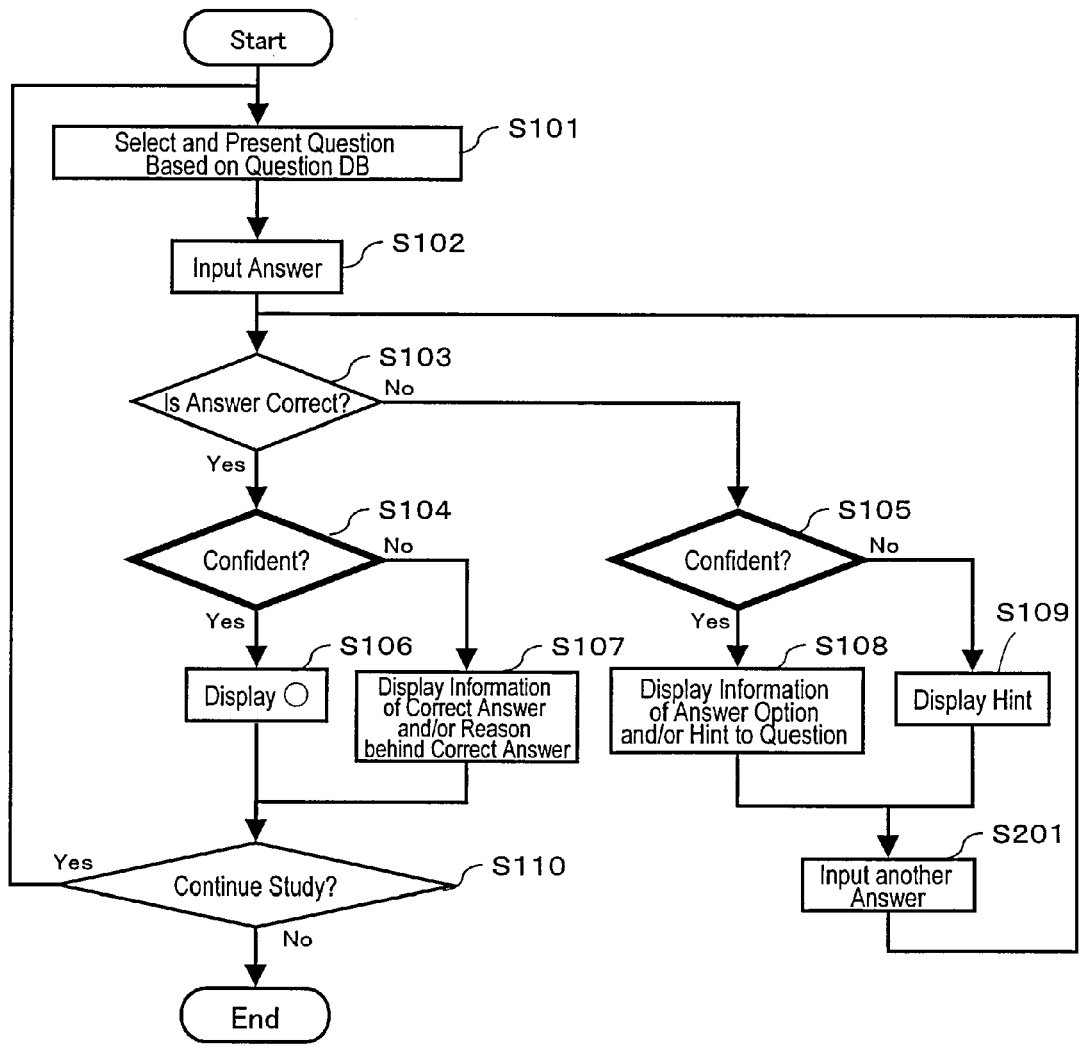
FIG. 8 A flowchart showing a procedure of processes by the service providing system 5, in which a process of inputting another answer is incorporated.

Note that, if the determination of step S103 finds that the answer is incorrect, processing may be performed so as to present a hint and then allow the user 10 to again answer the same question. FIG. 8 shows a procedure of processes by the service providing system 5 in which a process of inputting another answer is incorporated. A difference from the processing of FIG. 7 is the inclusion of step S201. Specifically, after a hint is presented at step S108 or step S109, control proceeds to step S201. Then, an operation of awaiting an answer input may occur so as to allow the user 10 to again answer the question at step S201. If an answer is input, the process returns to step S103, and processing is again performed with respect to that answer.

In FIG. 8, the steps other than steps S108, S109, and S201 are identical to the steps in FIG. 7. Therefore, the same step numbers are assigned thereto, and their descriptions are omitted.

As described above, with the service providing system 5 of the present embodiment, it becomes possible to automatically detect the degree of the user's confidence before making a correctness evaluation feedback, by constructing the service providing system 5 using the service providing apparatus 1. Based on the degree of the user's confidence and the correctness of the answer, the content for feedback can be changed in advance according to the user state, whereby the efficiency of studying is significantly improved.

For example, if the user has given the correct answer with confidence, processing may be performed without presenting unnecessary information or hints concerning the question. On the other hand, if the user has made the answer without confidence, information or hints can be presented only when information or hints are necessary, instead of making a feedback such as the result, or simultaneously with making a feedback. As a result, the efficiency of studying is significantly improved.

Note that, applications of the degree of confidence are not limited to the above, but the level of the question to be next asked may be changed based on the degree of the user's confidence. For example, with a method of lowering the level of the question if the degree of confidence is low and increasing the level of the question if the degree of confidence is high, etc., it becomes possible to ask questions that are suitable to the user's level.

6. Detailed Construction of the System According to Embodiment 2

Next, a service providing system and a service providing apparatus according to Embodiment 2 of the present invention will be described.

In the service providing system 5 according to Embodiment 1, the degree of the user's confidence with respect to an answer is determined, and information to be presented to the user is selected based on the degree of confidence and the correctness of the answer. However, the processing for each question is independent, and when the same question is to be asked, the question is not asked in such a manner as to reflect the previous answer result.

In the service providing system according to the present embodiment, by utilizing the degree of the user's confidence which is obtained through the same process as in the system of Embodiment 1, correct answers which are based on "Random Guess" and incorrect answers which are based on "Mistake" are determined, and such results are stored into a database. At a next time of asking, a question is selected and asked while considering the results up to that point. As a result, correct answers which are based on "Random Guess" can be identified in terms of insufficiently understood questions. Thus, the degree of understanding of the user can be measured, and by taking an appropriate measure such as presenting a review question, an efficient study can be realized.

Figures 9, 10:
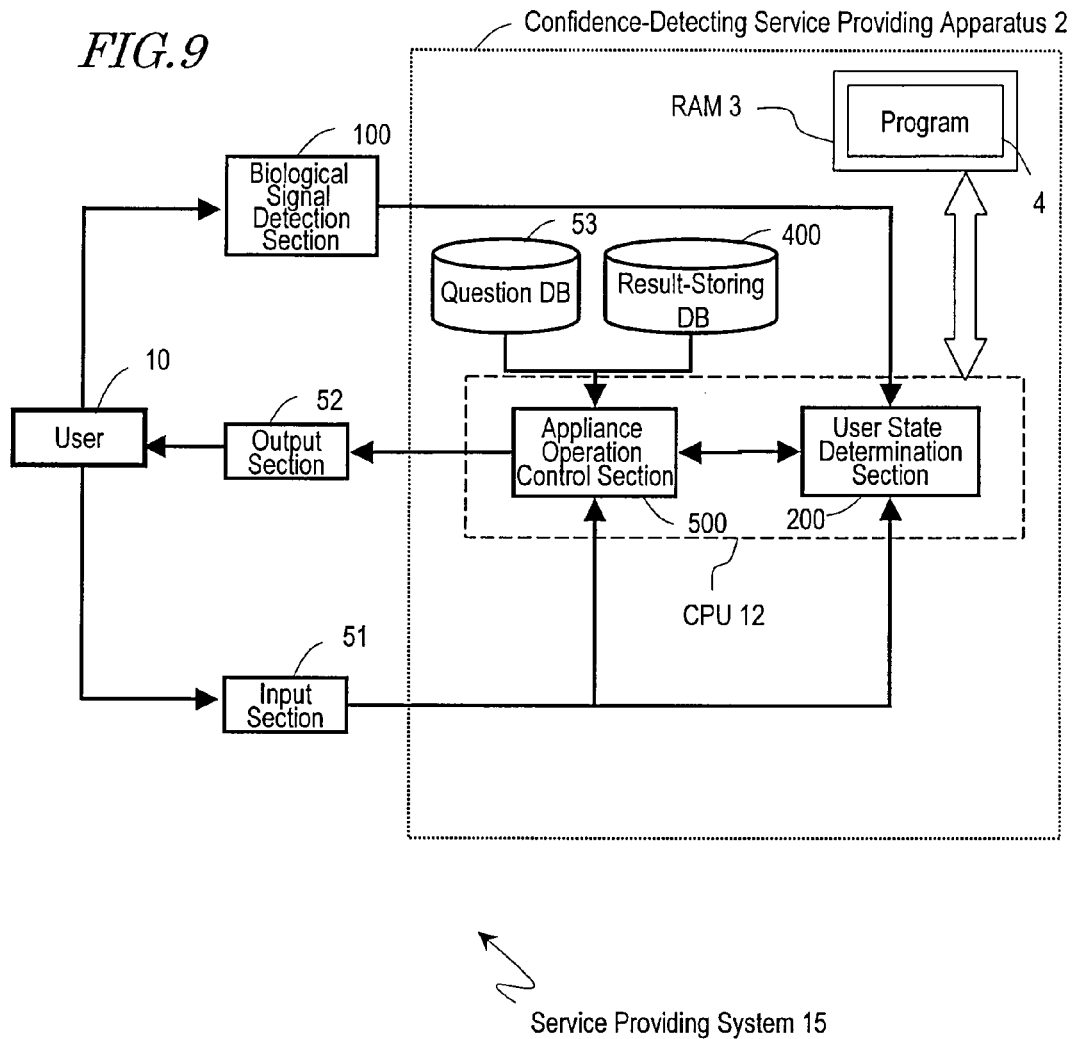
FIG. 9 A diagram showing the functional block construction of a service providing system 15 according to Embodiment 2.
FIG. 10 A diagram showing an example of a determination table.

FIG. 9 shows a functional block construction of the service providing system 15 according to the present embodiment. FIG. 9 also shows detailed functional blocks of the service providing apparatus 2. Note that the user block 10 is shown for convenience of description.

In FIG. 9, component elements which are identical to those in FIG. 2 are denoted by the same numerals, and descriptions thereof are omitted. The service providing apparatus 2 shown in FIG. 9 differs from the service providing apparatus 1 shown in FIG. 2 in that an appliance operation control section 500 which performs a different operation is comprised, and that a result-storing DB 400 is provided instead of a hint DB 300. Note that, since the content of the CPU 12 is unchanged, the same reference numeral is assigned thereto.

Hereinafter, the appliance operation control section 500 and the result-storing DB 400 will be described.

The appliance operation control section 500 receives the information of the degree of confidence of the user 10 as determined by the user state determination section 200, and determines the correctness of the answer of the user 10. Then, based on the degree of confidence information and the result of correctness, it determines the degree of understanding of the user 10 by referring to the determination table shown in FIG. 10.

FIG. 10 shows an example of the determination table. This table shows degrees of understanding that are identified based on correctness of the answer and the degree of confidence. The operation of the appliance operation control section 500 utilizing this table is as follows.

Specifically, if the answer of the user 10 is 'correct' and the degree of confidence of the user 10 indicates "Confident", it can be determined that the user has the best understanding. In this case, the appliance operation control section 500 makes an "Understood" determination from the determination table. If the answer of the user 10 is 'correct' and the degree of confidence of the user 10 indicates "Unconfident", it can be determined that the user has given the correct answer by random guessing. Therefore, the appliance operation control section 500 makes a "Random Guess" determination from the determination table. Thus, it can be determined whether a given correct answer is a correct answer based on "Random Guess" or not.

On the other hand, if the answer of the user 10 is 'incorrect' and the degree of confidence of the user 10 indicates "Confident", it is determined that the user has selected the incorrect answer by mistake. In this case, the appliance operation control section 500 makes a "Mistake" determination from the determination table. If the answer of the user 10 is 'incorrect' and the degree of confidence of the user 10 indicates "Unconfident", it can be determined that the user did not understand the content of the question. In this case, the appliance operation control section 500 makes a "Not Understood" determination from the determination table.

The appliance operation control section 500 causes the determination result using the aforementioned determination table to be stored to the result-storing DB 400. Moreover, the appliance operation control section 500 determines the question to be next presented, by referring to the question DB 53 and the result-storing DB 400.

The result-storing DB 400 is a database which is constructed on a hard disk drive, for example. The result-storing DB 400 retains a result table, in which the determination results by the appliance operation control section 500 are stored. FIG. 11 shows an example of a result table stored in the result-storing DB 400. In this table, the status of user's understanding (degree of understanding) with respect to each question, in the case where the question is asked more than once, is described.

7. Processes in the Service Providing System According to Embodiment 2

Next, with reference to the flowchart of FIG. 12, the overall flow of processes performed in the service providing system 15 of FIG. 9 will be described.

Figures 12, 13:
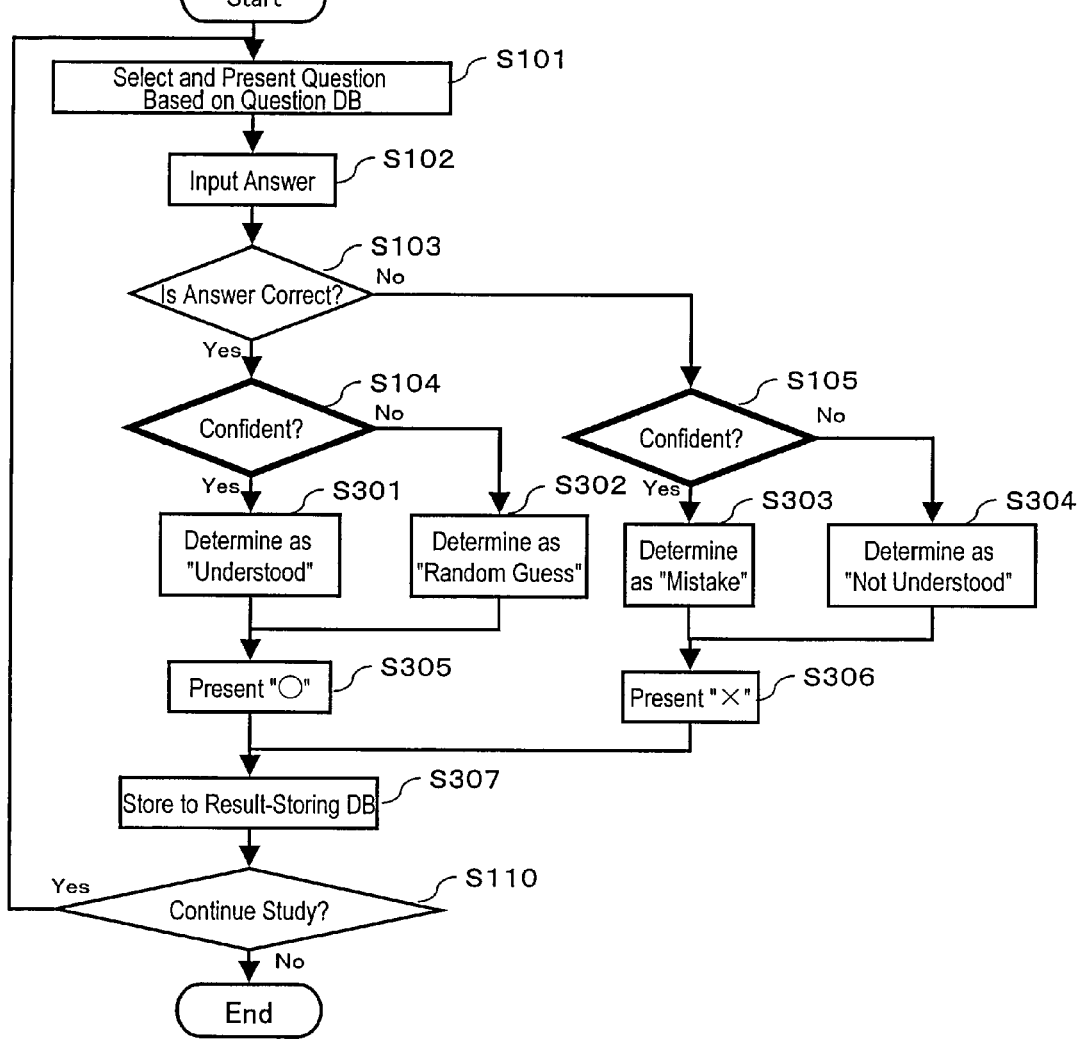
FIG. 12 A flowchart showing a procedure of processes by the service providing system 15 according to Embodiment 2.
FIG. 13 A diagram showing an example of a determination table, where the degrees of understanding are defined as weighting coefficients.

FIG. 12 shows a procedure of processes by the service providing system 15 of the present embodiment. Any step where the same process as in FIG. 7 is performed is denoted by the same numeral, and the description thereof is omitted. Firstly, step S101 to step S105 are the same as the processes in FIG. 7.

All of the following step S301 to step S304 are processes where, the appliance operation control section 500 determines the degree of understanding of the user 10 by using the determination table shown in FIG. 10.

At step S301, which is followed when the answer is 'correct' and 'confident', the appliance operation control section 500 determines that the user 10 has "Understood" the question. On the other hand, at step S302, which is followed when the answer 'correct' and 'unconfident', the appliance operation control section 500 determines that the user 10 has given the correct answer to the question based on "Random Guess". After steps S301 and S302, the process proceeds to step S307.

At step S303, which is followed when the answer is 'incorrect' and 'confident', the appliance operation control section 500 determines that the user 10 has "Mistaken" the question. On the other hand, at step S304, which is followed when the answer is 'incorrect' and 'unconfident', the appliance operation control section 500 determines that the user 10 has "Not Understood" the question. After steps S303 and S304, the process proceeds to step S306.

At step S305, the appliance operation control section 500 feeds back to the user 10 that the answer of the user 10 was correct, via the output section 52. For example, in the case where the output section 52 is a display, the appliance operation control section 500 displays only "○", which indicates 'correct'.

On the other hand, at step S306, the appliance operation control section 500 feeds back to the user 10 that the answer of the user 10 was incorrect, via the output section 52. In the case where the output section 52 is a display, for example, the appliance operation control section 500 displays "X", which indicates 'incorrect'.

However, as will be seen from the waveform of FIG. 19, in order to determine the degree of confidence from the event-related potential, a time lag of about 1000 ms is observed from the answer input at step S102 until the feedback content is output at step S305 or S306.

At step S307, the result-storing DB 400 receives the determination result from the appliance operation control section 500, and stores it in the result table. As the method of storing the determination results may be, as shown in FIG. 11, for example, labels indicating "Understood", "Random Guess", "Mistake", or "Not Understood" may be stored for each question.

As a result, the order of questions to be next asked at step S101 can be determined based on the labels. For example, among the labels of the user's degree of understanding stored in the result-storing DB 400, questions may be selected in the order of e.g., "Not Understood", "Random Guess", "Mistake", "Understood".

Note that the degrees of understanding may be stored as weighting coefficients. For example, FIG. 13 shows an example of a determination table where the degrees of understanding are defined as weighting coefficients. In this table, a weighting coefficient of 0.1 is assigned when the understanding is sufficient ("correct"), and a weighting coefficient of 3 is assigned when the understanding of the user 10 is insufficient ("Random Guess" "Mistake" "Not Understood").

By assigning such weighting coefficients, when selecting questions for review, it is possible to select with priority those questions which were not sufficiently understood. In other words, in the selection of questions at step S101, by asking the questions having large numerical values in the result table first, it becomes possible to intensively cover the important questions which were not sufficiently understood by the user. The value of a weighting coefficient serves as a parameter to increase the probability that a similar question will be again selected for review.

Note that, the hint DB 300 (which is a component element of Embodiment 1) may be added for presentation to the user 10 in accordance with the degree of understanding, instead of providing a correctness evaluation, or simultaneously with providing a correctness evaluation.

According to the present embodiment, by using the confidence-detecting service providing apparatus, the degree of the user's confidence with respect to an answer can be automatically detected. As a result, answer results which were conventionally recognizable only in the two statuses of "correct" and "incorrect" become distinguishable into the four statuses of "Understood", "Random Guess", "Mistake", and "Not Understood". Thus, the correct answers based on "Random Guess", which were conventionally determined as "Understood" and overlooked, can now be determined as insufficiently understood, and be followed by presentation of review questions. Since appropriate measures can be surely taken with regard to the insufficiently understood questions, the efficiency of studying is greatly improved.

One table as shown in FIG. 11 may be provided for a plurality of users, or provided for each user. In the case where one table is provided for a plurality of users, the questions which are insufficiently understood by many users are identified, which makes it easier to give alarms or present countermeasures for the questions to the entire body of users. On the other hand, in the case where one table is provided for each user, it is possible to realize a careful asking which is tailored according to the degree of understanding of each user, etc. In either example, the efficiency of studying can be greatly improved with respect to all of the users.

8. Detailed Construction of the System According to Embodiment 3

Next, a service providing system and a service providing apparatus according to Embodiment 3 of the present invention will be described.

The service providing systems according to Embodiments 1 and 2 are realized as study systems, backed by the experimental results described earlier. In each study system, the degree of confidence of a user who has answered a study question is determined with respect to the answer, and information to be presented to the user is selected based on the degree of confidence and the correctness of the answer.

However, the above-described experimental results are also applicable to systems other than study systems. For example, utilizing the above-described experimental results will make it possible, when a user has manipulated an electronic appliance such as a DVD recorder, to determine the degree of the user's confidence with respect to the manipulation, before the appliance operation is begun. The "degree of the user's confidence" as used herein represents whether the user feels that he or she has been able to manipulate the electronic appliance so as to execute a desired operation. Since there is a time lag of generally about 1 second from the input of an instruction by a user manipulation (hereinafter referred to as a "manipulation input") to the start of the appliance operation, this time lag can be utilized for measuring the SPN component of an event-related potential, from the manipulation input as a starting point. As a result, the degree of confidence can be determined based on the SPN component, similarly to Embodiments 1 and 2.

To explain correspondence with the above-described experiment, "presentation of a question" in the earlier-described experiment corresponds to the user imaging a desired appliance operation when manipulating the electronic appliance. On the other hand, the "answer input" corresponds to a manipulation input via a remote control button or the like.

As the electronic appliance selectively switches between presenting and not presenting a help message in accordance with the presence or absence of confidence which is indicated by the degree of confidence, a service providing system concerning help indications is realized.

For example, in response to a manipulation for which there is a high degree of confidence, i.e., a confident manipulation, the service providing system performs an operation which corresponds to that manipulation, without presenting helps or prospective appliance operations. On the other hand, in response to a manipulation for which there is a low degree of confidence, i.e., an unconfident manipulation, a help or a prospective appliance operation is presented. Since a switching is made between presenting and not presenting a help message or the like based on the degree of confidence, the user does not need to spontaneously press a help button on the remote control. As a result, instead of bothering the user, it is possible to assist in the user's manipulation input, whereby the ease of use of the appliance is improved.

Hereinafter, a service providing system which is realized as a help indication system will be described.

Figure 14:
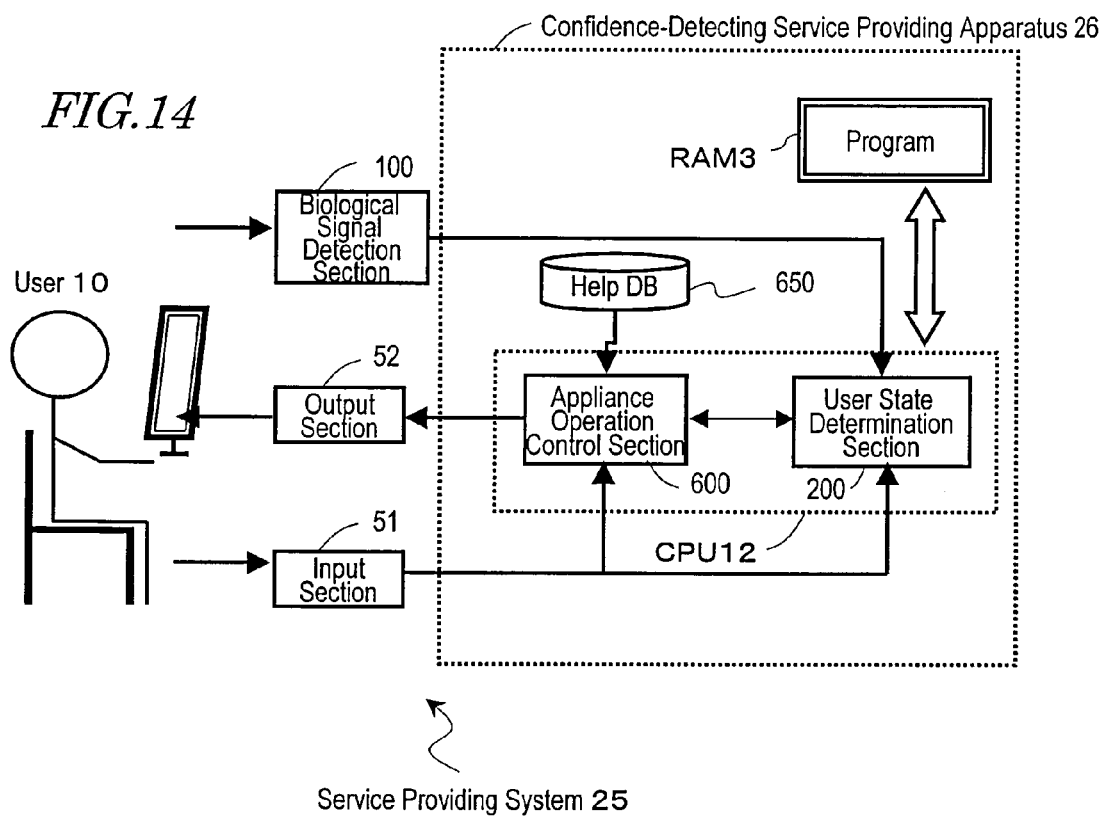
FIG. 14 A diagram showing the functional block construction of a service providing system 25 according to Embodiment 3.

FIG. 14 shows a functional block construction of the service providing system 25 according to the present embodiment. FIG. 14 also shows detailed functional blocks of the service providing apparatus 26. Note that the user block 10 is shown for convenience of description.

In FIG. 14, component elements which are identical to those in FIG. 2 are denoted by the same numerals, and descriptions thereof are omitted. The service providing apparatus 26 shown in FIG. 14 differs from the service providing apparatus 1 shown in FIG. 2 in that a question DB 53 is not comprised, an appliance operation control section 600 which performs a different operation is comprised, and that a help DB 650 is provided instead of a hint DB 300. Note that, since the content of the CPU 12 is unchanged, the same reference numeral is assigned thereto.

Hereinafter, the appliance operation control section 600 and the help DB 650 will be described. As a premise, it is assumed that the user state determination section 200 receives a manipulation input of the user 10 via a remote control or the like serving as the input section 51, and determines the degree of the user's confidence based on the SPN component of an event-related potential, which is measured by the biological signal detection section 100 from the receiving timing as a starting point.

From the user state determination section 200, the appliance operation control section 600 receives information of the degree of confidence of the user 10 with respect to the manipulation input. If the received information indicates "Confident", the appliance operation control section 600 instructs the other component elements in the service providing apparatus 26 to operate in accordance with the content of the manipulation input. On the other hand, if the received information indicates "Unconfident", the appliance operation control section 600 refers to the help DB 650, and presents a help concerning a function which can be realized with the manipulation button that has been used for the input, for example, instead of an appliance operation which is in accordance with the manipulation input.

Alternatively, as appliance operations to be realized with the manipulation button that has been used for the input, a prospective appliance operation which is functionally similar may be presented, e.g., "Did you mean . . . ?". Two or more prospective appliance operations may be presented so as to be selected by the user. Note that the prospective appliance operations to be presented can be stored in the help DB 650. The ordinal ranks of prospects may be determined based on the manipulation history, personal preferences, or the like of the user.

The help DB 650 is a database in which input contents and explanations concerning functions of the service providing system 25 are stored in association. An input content is, for example, the name of a button which has been pressed in connection with a manipulation input. Functions of the service providing system 25 are the functions of the service providing apparatus 26, which more specifically is implemented as a DVD recorder having a built-in HDD, or the like. The help DB 650 is constructed on a hard disk drive, for example. Based on the determination result by the appliance operation control section 600, it is determined whether or not the help DB 650 is referred to.

Note that the help DB 650 may store a plurality of prospective explanations of appliance operations for each button name related to one manipulation input.

FIGS. 15(a) and (b) show examples of the help DB 650 in the case where the confidence-detecting service providing apparatus 26 is a DVD recorder. FIG. 15(a) shows an example of the case where a help concerning a manipulation input button is presented for each manipulation input button; and FIG. 15(b) shows an example of the case where a plurality of prospective appliance operations are presented for each manipulation input button.

9. Processes in the Service Providing System According to Embodiment 3

Next, with reference to the flowchart of FIG. 16, the overall flow of processes performed in the service providing system 25 of FIG. 14 will be described.

Figure 16:
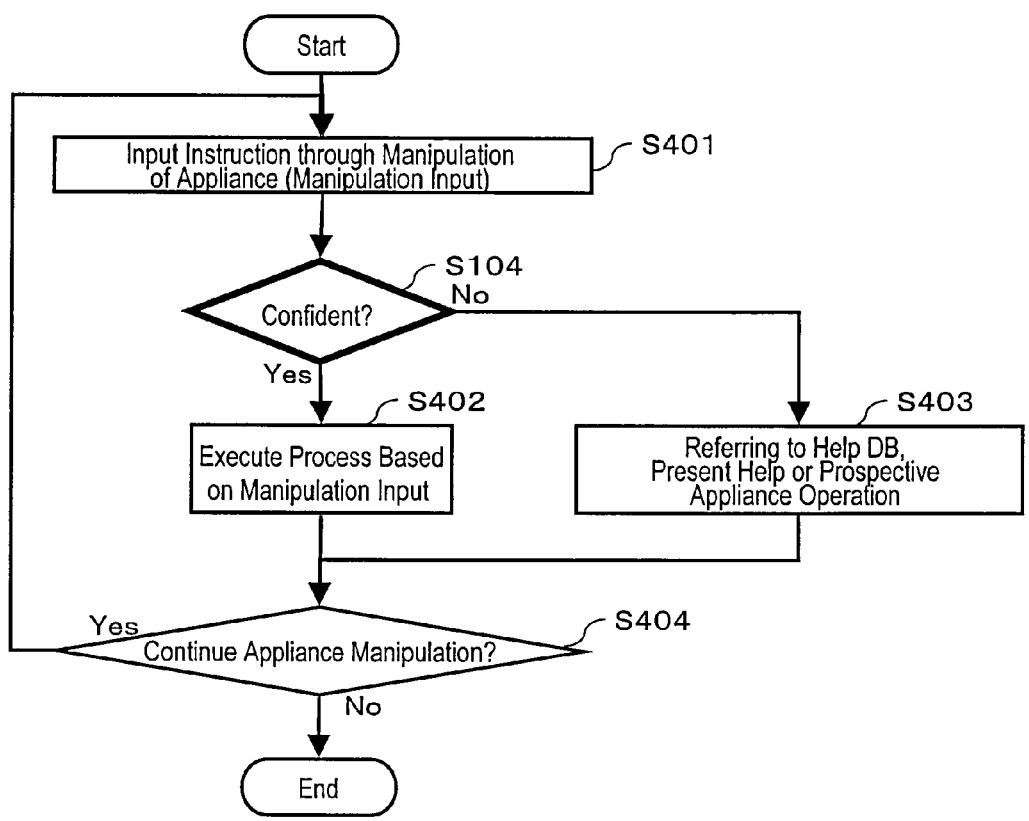
FIG. 16 A flowchart showing a procedure of processes by the service providing system 25 according to the embodiment.
Figure 17:
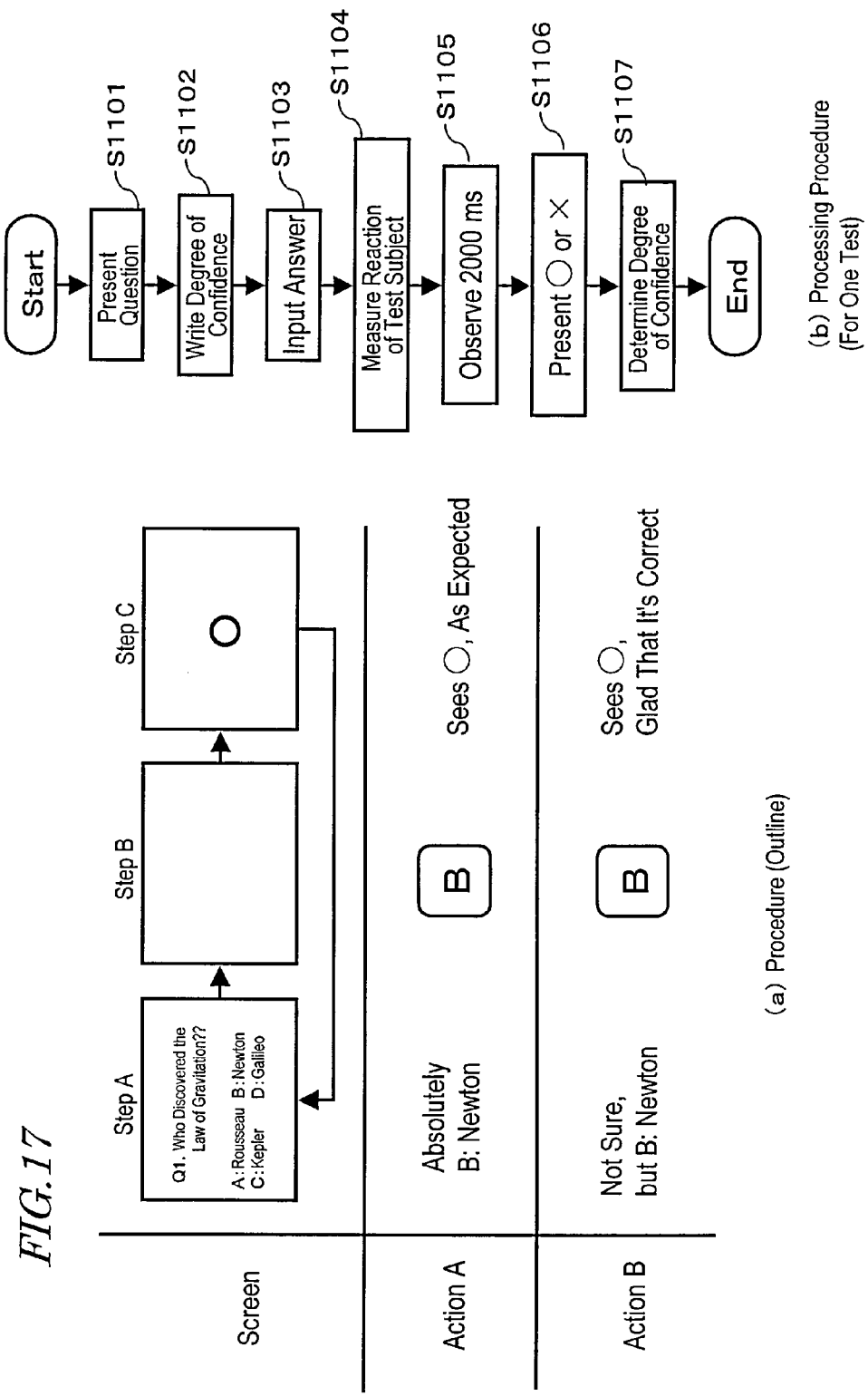
FIG. 17 (a) is a diagram showing the outline of an experimental procedure; and (b) is a flowchart showing a procedure corresponding to one test.

FIG. 16 shows a procedure of processes by service providing system 25 of the present embodiment. Step S104, where the same process as in FIG. 7 is performed, is denoted by the same numeral and the description thereof is omitted.

At step S401, when the user 10 inputs an instruction via the input section 51, the service providing apparatus 26 receives this manipulation input.

At step S104, the user state determination section 200 determines the presence or absence of confidence. If the user state determination section 200 makes a 'confident' determination, the process proceeds to step S402; if it makes an 'unconfident' determination, the process proceeds to step S403.

At step S402, the appliance operation control section 600 performs a process based on the manipulation input. User assistances such as helps are not particularly given because the user is confident that his or her manipulation is appropriate as a manipulation for the desired operation.

On the other hand, at step S403, the appliance operation control section 600 refers to the help DB 650 and displays a help which corresponds to the manipulation input, or presents prospective appliance operations corresponding to the manipulation input.

For example, suppose that the help DB 650 as shown in FIG. 15(a) is provided. If the user state determination section 200 makes an 'unconfident' determination with respect to a press of a program guide button, the appliance operation control section 600 reads the help DB 650, and displays "Allows you to confirm content of program scheduled to be broadcast", which is an explanation of a function of the program guide button.

Alternatively, suppose that the help DB 650 as shown in FIG. 15(*b*) is provided. If the user state determination section 200 makes an 'unconfident' determination with respect to a press of the program guide button, the appliance operation control section 600 selects and reads at least one of candidates 1 to 3 in the help DB 650. For example, if candidate 1 is read, "Press program guide button to display list of programs scheduled to be broadcast" is displayed corresponding to candidate 1.

The appliance operation control section 600 may read candidates 2 and 3, simultaneously with or consecutively from candidate 1. When candidate 2 is read, the appliance operation control section 600 displays "Press play back navigation to display a list of recorded programs". When candidate 3 is read, the appliance operation control section 600 may display "Press search button to search for recommended programs". The order of reading the candidates may be determined as appropriate. For example, if ordinal ranks for being read are set based on candidate numbers, the appliance operation control section 600 may selectively read the corresponding explanations in the order of candidate numbers.

At step S404, based on the presence or absence of a next manipulation input from the user, or the presence or absence of a press of a back button or a press of a cancel button indicating that the manipulation is to be discontinued, the appliance operation control section 600 determines whether the user 10 will continue appliance manipulations or not. If it is determined that appliance manipulations will be continued, the process is repeated from step S401. Based on a subsequent manipulation input, the appliance operation control section 600 gives instructs that a function be executed. On the other hand, if the appliance operation control section 600 determines that the user will not continue appliance manipulations, it ends the process.

Note that, as will be seen from the waveform of FIG. 19, the determination process of step S104 where the degree of confidence is determined based on an event-related potential is preferably such that a time lag of about 1000 ms seconds is observed from the manipulation input at step S401 to the start of an appliance operation at step S402 or S403. If it is possible to observe a time lag of about 2000 ms from the manipulation input to the start of an appliance operation, the degree of confidence can be more accurately determined.

According to the present embodiment, by using the confidence-detecting service providing apparatus, the degree of a user's confidence with respect to a manipulation input can be automatically detected. The degree of confidence of the user with respect to a manipulation input when performing an appliance manipulation, which was conventionally unknown, becomes distinguishable into the two states of "Confident" and "Unconfident". As a result, in accordance with the degree of confidence, the appliance operation can be changed in advance, e.g., by presenting helps or prospective appliance operations in response to an unconfident manipulation. Since it becomes possible to assist in the user's manipulation input without bothering the user, the ease of use of the appliance is improved.

INDUSTRIAL APPLICABILITY

An information processing apparatus and an information processing system according to the present invention can be adopted in appliances that, through exchanges of information with the user, provide services which are in accordance with a user. For example, in a situation where an answer input of a user with respect to a presented question is clearly correct or incorrect, the degree of the user's confidence with respect to the answer can be determined automatically and before a correctness evaluation is fed back. Alternatively, a degree of a user's confidence representing whether the user feels that he or she has been able to manipulate an electronic appliance so as to execute a desired operation can be determined before the operation of the appliance is started. Since the content of the operation can be appropriately selected in accordance with the degree of confidence, it becomes possible to assist in the user's manipulation input without bothering the user, whereby the ease of use of the appliance is improved. In particular, this can be applied in a study system or a help indication system of an electronic appliance, thus providing a drastically improved studying effect. It can also be utilized for usability evaluation purposes.

The invention claimed is:

1. An information processing system comprising:
   an input section for receiving an input from a user;
   a signal detection section for measuring a signal concerning an event-related potential of electroencephalograms of the user;
   a determination section for determining a degree of confidence of the user with respect to the input based on an amount of negative shift in voltage in the measured event-related potential of electroencephalograms of the user during a predetermined period, the predetermined period being subsequent to a receipt of the input from the user;
   a control section for determining a content to be presented based on the degree of confidence; and
   an output section for presenting the determined content.

2. The information processing system of claim 1, wherein, the output section presents a question to the user;
   as the input, the input section receives an answer of the user to the question which is output by the output section;
   based on the degree of confidence, the control section determines to present information related to the question or related to a correct answer thereto; and
   the output section presents the information after lapse of the predetermined period.

3. The information processing system of claim 1, wherein the determination section determines the degree of confidence of the user by defining as the predetermined period a period within about 2000 milliseconds starting from a point in time of receiving the input.

4. The information processing system of claim 2, further comprising a database storing information related to the question and related to the correct answer, wherein,
   the control section determines correctness of the answer of the user by referring to the database, and based on the degree of confidence of the user and a determination result of correctness, selects the information related to the question or related to the correct answer thereto.

5. The information processing system of claim 4, wherein, the database stores information of a plurality of hints related to the correct answer; and
   the control section selects from among the hints based on the degree of confidence of the user and the determination result of correctness.

6. The information processing system of claim 4, wherein the control section outputs information representing a degree of understanding of the user, based on the degree of confidence of the user and the determination result of correctness.

7. The information processing system of claim 1, wherein,
the amount of negative shift in voltage in the event-related potential has a corresponding relationship with a gradient of a waveform of negative shift in voltage; and
the determination section retains a threshold which falls between a gradient value of negative shift in voltage corresponding to 'confident' and a gradient value of negative shift in voltage corresponding to 'unconfident', and
by comparing a gradient of a waveform of the acquired event-related potential against the threshold, makes a 'confident' determination if the gradient of the waveform is smaller than the threshold, and makes an 'unconfident' determination if the gradient of the waveform is larger than the threshold, and outputs information representing the determination result to the control section.

8. The information processing system of claim 1, wherein,
the amount of negative shift in voltage in the event-related potential has a corresponding relationship with a gradient of a waveform of negative shift in voltage; and
the determination section includes a table which retains first numerical values representing a gradient of negative shift in voltage corresponding to 'confident' and second numerical values representing a gradient of negative shift in voltage corresponding to 'unconfident', the first numerical values and the second numerical values being previously acquired through an experiment, and
based on a Mahalanobis distance between a gradient value of a waveform of the acquired event-related potential and the first numerical values and on a Mahalanobis distance between a gradient value of the waveform of the acquired event-related potential and the second numerical values, outputs information representing the determination result to the control section.

9. The information processing system of claim 1, further comprising a database in which input content and explanations concerning functions of the information processing system are stored in association, wherein,
in accordance with the degree of confidence, the control section refers to the database and selects an explanation which is associated with the input from the user; and
the output section presents the selected explanation after lapse of the predetermined period.

10. The information processing system of claim 9, wherein the determination section determines presence or absence of confidence of the user with respect to the input by defining as the predetermined period a period within about 2000 milliseconds starting from a point in time of receiving the input.

11. The information processing system of claim 10, wherein, the control section refers to the database when the determination section determines that the user is unconfident.

12. The information processing system of claim 9, wherein,
a plurality of prospective explanations are stored in association with each input content in the database; and
the control section selects at least one of the plurality of prospective explanations.

13. The information processing system of claim 12, wherein,
ordinal ranks are set for the plurality of prospective explanations in the database; and
the control section selects from among the plurality of prospective explanations in accordance with the ordinal ranks.

14. The information processing system of claim 9, wherein,
after the output section presents the explanation, the input section further receives an input from the user; and
the control section instructs that a function be executed based on the further received input.

15. An information processing apparatus for being connected to: an input device which receives an input from a user; an output device which presents information to the user; and a signal detection device which measures a signal concerning an event-related potential of electroencephalograms of the user, the information processing apparatus comprising:
a determination section for determining a degree of confidence of the user with respect to the input based on an amount of negative shift in voltage in the measured event-related potential of electroencephalograms of the user during a predetermined period, the predetermined period being subsequent to a receipt of the input from the user;
a control section for determining a content to be presented to the user based on the degree of confidence, and transmitting the determined content to the output section after lapse of the predetermined period,
wherein the output section presents the content.

16. An information processing method comprising the steps of:
receiving an input from a user;
measuring a signal concerning an event-related potential of electroencephalograms of the user;
determining a degree of confidence of the user with respect to the input based on an amount of negative shift in voltage in the measured event-related potential of electroencephalograms of the user during a predetermined period, the predetermined period being subsequent to a receipt of the input from the user;
determining a content to be presented to the user based on the degree of confidence; and
presenting the determined content.

17. The information processing system of claim 1, wherein,
the amount of negative shift in voltage is an amount representing a gradient of a wave form of the event-related potential measured from a start time point to an end time point,
the start time point being a time point when the input is received from the user,
the end time point being a time point after lapse of a predetermined period from the start time point.

18. An information processing system comprising:
an output section for presenting a question to a user;
an input section for receiving an answer of the user to the question which is presented by the output section;
a signal detection section for measuring a signal concerning an event-related potential of electroencephalograms of the user;
a determination section for determining a degree of confidence of the user with respect to the input based on an amount of negative shift in voltage in the measured event-related potential of electroencephalograms of the user during a predetermined period, the predetermined period being subsequent to a receipt of the input from the user; and
a control section for determining a content to be presented based on the degree of confidence, wherein
the output section presents the determined content.

* * * * *

UNITED STATES PATENT AND TRADEMARK OFFICE
CERTIFICATE OF CORRECTION

| | | |
|---|---|---|
| PATENT NO. | : 7,945,865 B2 | Page 1 of 1 |
| APPLICATION NO. | : 11/718108 | |
| DATED | : May 17, 2011 | |
| INVENTOR(S) | : Shinobu Adachi et al. | |

It is certified that error appears in the above-identified patent and that said Letters Patent is hereby corrected as shown below:

Title Page, under "OTHER PUBLICATIONS" line 6, "Psychophysiololgy" should read
-- Psychophysiology --.

Signed and Sealed this

Thirteenth Day of September, 2011

David J. Kappos
*Director of the United States Patent and Trademark Office*

UNITED STATES PATENT AND TRADEMARK OFFICE
CERTIFICATE OF CORRECTION

| | |
|---|---|
| PATENT NO. | : 7,945,865 B2 |
| APPLICATION NO. | : 11/718108 |
| DATED | : May 17, 2011 |
| INVENTOR(S) | : Shinobu Adachi and Koji Morikawa |

It is certified that error appears in the above-identified patent and that said Letters Patent is hereby corrected as shown below:

Title Page, under Primary Examiner, "Tadeese" should read -- Tadesse --.

Signed and Sealed this
Twenty-second Day of November, 2011

David J. Kappos
*Director of the United States Patent and Trademark Office*

UNITED STATES PATENT AND TRADEMARK OFFICE
CERTIFICATE OF CORRECTION

PATENT NO. : 7,945,865 B2
APPLICATION NO. : 11/718108
DATED : May 17, 2011
INVENTOR(S) : Shinobu Adachi et al.

It is certified that error appears in the above-identified patent and that said Letters Patent is hereby corrected as shown below:

Title Page, under "OTHER PUBLICATIONS"

add the following publications:

-- Takeo IIDA; "Multimedia no Tame no Hinshitsu Hyoka (final time) Kansei no Kyakkanteki Keisoku to Human Interface Hyoka," Eizo Joho Media Gakkaishi, Vol. 54, No. 12; 20 December 2000; page 1716(56), right column, line 5 to page 1717(57), left column, line 21. (Listed on International Search Report for Corresponding Application No. PCT/JP2006/320102 submitted on April 27, 2007) --;

-- Edited by Hiroshi TAMURA; "Human Interface," first edition, Ohmsha, Ltd.; 30 May 1998; page 60, right column, line 18 to page 61, right column, line 15. (Listed on International Search Report for Corresponding Application No. PCT/JP2006/320102 submitted on April 27 2007) --; and -- Edited by National Institute of Advanced Industrial Science and Technology, Institute for Human Science and Biomedical Engineering; "Ningen Keisoku Handbook," first edition, Kabushiki Kaisha Asakura Shoten; 01 September 2003; page 73, left column, line 30 to right column, line 3; page 74, right column, lines 9 to 24. (Listed on International Search Report for Corresponding Application No. PCT/JP2006/320102 submitted on April 27, 2007) --.

Signed and Sealed this
Third Day of April, 2012

David J. Kappos
*Director of the United States Patent and Trademark Office*